United States Patent
Le et al.

(10) Patent No.: US 12,310,726 B1
(45) Date of Patent: May 27, 2025

(54) SYSTEM AND METHOD FOR ROBUST PULSE OXIMETRY USING IMAGE RECONSTRUCTION

(71) Applicant: Apple Inc., Cupertino, CA (US)

(72) Inventors: Mai Tuyet Le, Sunnyvale, CA (US); Xiao Jin, San Ramon, CA (US); Paul D. Mannheimer, Los Altos, CA (US); Albert E. Cerussi, San Jose, CA (US); Sankalita Saha, Saratoga, CA (US)

(73) Assignee: Apple Inc., Cupertino, CA (US)

( * ) Notice: Subject to any disclaimer, the term of this patent is extended or adjusted under 35 U.S.C. 154(b) by 752 days.

(21) Appl. No.: 17/472,340

(22) Filed: Sep. 10, 2021

Related U.S. Application Data

(60) Provisional application No. 63/077,241, filed on Sep. 11, 2020.

(51) Int. Cl.
*A61B 5/1455* (2006.01)

(52) U.S. Cl.
CPC ................ *A61B 5/14551* (2013.01)

(58) Field of Classification Search
CPC . A61B 5/0205; A61B 5/1455; A61B 5/14551; A61B 5/14552; A61B 5/14532; A61B 5/14535; A61B 5/14539; A61B 5/14542; A61B 5/14546; A61B 5/14553; A61B 5/14556
See application file for complete search history.

(56) References Cited

U.S. PATENT DOCUMENTS

| | | | |
|---|---|---|---|
| 8,463,006 B2 | 6/2013 | Prokoski | |
| 10,004,403 B2 | 6/2018 | DeBernardis et al. | |
| 10,105,090 B2 | 10/2018 | Barbour et al. | |
| 2002/0033454 A1* | 3/2002 | Cheng | A61B 5/14546 250/339.12 |
| 2016/0235373 A1* | 8/2016 | Sharma | G16H 10/40 |
| 2017/0055842 A1* | 3/2017 | Umezawa | A61B 5/0095 |

\* cited by examiner

*Primary Examiner* — Chu Chuan Liu
(74) *Attorney, Agent, or Firm* — Kubota & Basol LLP

(57) ABSTRACT

A characteristic (e.g., SpO2) of a user's physiological signals can be estimated using a pulse oximeter. In some examples, inconsistent measurement of the physiological characteristic may occur despite the underlying physiological signals having quality characteristics consistent with physiologically valid signals showing a consistent cardiac signal indicative of accurate measurement of the physiological characteristic. In particular, the measurement inconsistency may be associated with a spatially localized region. Such measurement inconsistency may result in an incorrect, low estimate of the physiological characteristic relative to the true characteristic (e.g., the SpO2 estimate may skew lower than the true SpO2). An algorithm may be used to detect spatially localized measurement inconsistency and to mitigate or reduce its effect to improve the accuracy of the estimate of the physiological characteristic.

20 Claims, 15 Drawing Sheets

PHOTOPLETHYSMOGRAPHY (PPG) SIGNAL

SYSTEM AND METHOD FOR ROBUST PULSE OXIMETRY USING IMAGE RECONSTRUCTION

CROSS-REFERENCE TO RELATED APPLICATIONS

This application claims the benefit of U.S. Provisional Application No. 63/077,241, filed Sep. 11, 2020, the content of which is incorporated herein by reference in its entirety for all purposes.

FIELD OF THE DISCLOSURE

This relates generally to pulse oximetry systems and methods, and more particularly, to pulse oximetry systems and methods utilizing image reconstruction and detection of spatially localized measurement inconsistency to improve robustness of pulse oximetry measurements.

BACKGROUND OF THE DISCLOSURE

Information or characteristics (e.g., pulse rate or arterial oxygen saturation) of a user's physiological signals can be determined by pulse oximetry systems and methods. In a basic form, pulse oximetry systems and methods can utilize one or more light emitters to illuminate a user's tissue and one or more light detectors to receive light that enters and probes a subsurface volume of tissue. The light emitters and light detectors can be in contact with the tissue or can be remote (i.e., not in contact) to the tissue surface. For example, arterial oxygen saturation can be estimated based on a perfusion index ratio for two different wavelengths of light. However, the estimates of information or characteristics of a user's physiological signals may be inaccurate when the light emitters or light detectors are not in good contact, the light emitters or detectors are oriented differently with respect to the tissue surface than expected, there are other anomalies in the path of light from light emitters to light detectors, or under other conditions that results in measurements that are incompatible with assumptions of pulse oximetry.

SUMMARY OF THE DISCLOSURE

This relates to systems and methods for robust estimation of a characteristic of a user's physiological signals. For example, the physiological characteristic can be oxygen saturation of the hemoglobin in arterial blood (SpO2) as estimated by a pulse oximeter (SpO2). In some examples, inconsistent measurement of the physiological characteristic (e.g., SpO2) may occur (e.g., relative to a user's true SpO2) despite the underlying physiological signals (e.g., photoplethysmogram signals measured using an optical sensor) having quality characteristics consistent with physiologically valid signals showing a consistent cardiac signal indicative of accurate measurement of the physiological characteristic. In particular, the measurement inconsistency may be associated with a spatially localized region (e.g., corresponding to some measurement channel(s) of an electronic device and/or the underlying tissue measured by the channel(s)), referred to herein as a "spatially localized measurement inconsistency." Such measurement inconsistency may result in an incorrect, low estimate of the physiological characteristic relative to the true characteristic (e.g., an SpO2 estimate may skew lower than the true SpO2). Thus, spatially localized measurement inconsistency can make accurate estimation of SpO2 difficult, especially measurements at certain areas of the body (e.g., at the wrist). As described herein, an algorithm may be used to detect spatially localized measurement inconsistency (e.g., inconsistency above a threshold) and to mitigate or reduce its effect to improve the accuracy of the estimate of the physiological characteristic. Such an algorithm may be referred to herein as a "measurement inconsistency mitigation algorithm."

DETAILED DESCRIPTION

Figure 1A:
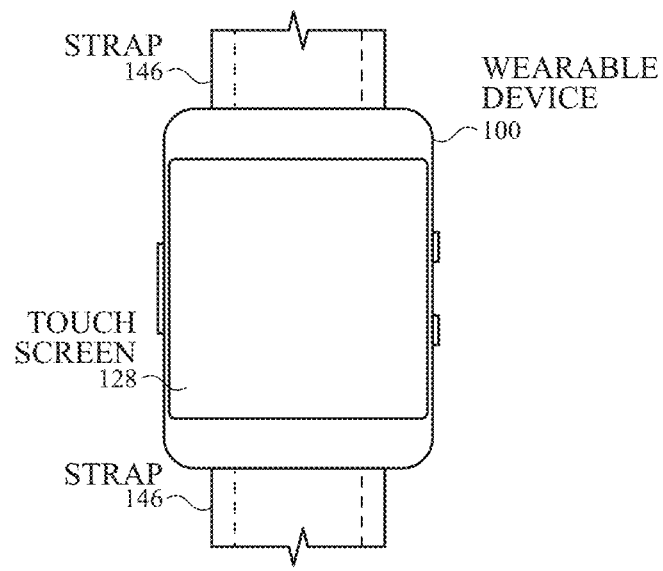
FIGS. 1A-1B illustrate views of an exemplary electronic device including one or more optical sensors according to examples of the disclosure.

In the following description of examples, reference is made to the accompanying drawings which form a part hereof, and in which it is shown by way of illustration specific examples that are optionally practiced. It is to be understood that other examples are optionally used and structural changes are optionally made without departing from the scope of the disclosed examples.

This relates to systems and methods for robust estimation of a physiological characteristic (e.g., arterial blood oxygen saturation) using a user's physiological signals. As used herein, physiological signals refer to signals generated by a physiological sensor (e.g., a photoplethysmogram (PPG) signal) that can be used for estimating the physiological characteristic (or condition) of a patient or user. A user's physiological signals can be determined by measurements using pulse oximetry systems. Such pulse oximetry systems can be designed to be sensitive to changes in the red blood cell number/concentration, volume, or blood oxygen state included in the sample or a user's vasculature. In a basic form, pulse oximetry systems can employ a light emitter (or plurality thereof) that injects light into the user's tissue and a light detector (or plurality thereof) to receive light that reflects and/or scatters and exits the tissue. In some examples, at least a portion of the photon path length interacts with tissue subsurface structures. Pulse oximetry systems can include, but are not limited to, arterial blood oxygen saturation estimation systems (SpO2 systems) configured to capture optical signals such as PPG signals. SpO2 systems can estimate a characteristic of physiological signals based on the attenuation of light (as measured by a physiological signal sensor) that varies over the duration of the cardiac cycle. Attenuation can be due to absorption, and/or scattering resulting from physiological/mechanical changes. Physiological/mechanical changes can include, but are not limited to, red blood cell number, cell/blood volume, red blood cell orientation, red blood cell/blood velocity, shear force, location/spatial distribution, concentration in the tissue, or other tissue properties (e.g., hydration, etc.), or a combination thereof. The estimated characteristics of the physiological signals (e.g., derive from the PPG signals) can include SpO2, heart rate, etc.

In some examples, inconsistent measurement of the physiological characteristic (e.g., SpO2) may occur (e.g., relative to a user's true SpO2) despite the underlying physiological signals (e.g., photoplethysmogram signals measured using an optical sensor) having quality characteristics consistent with physiologically valid signals showing a consistent cardiac signal indicative of accurate measurement of the physiological characteristic. In particular, the measurement inconsistency may be associated with a spatially localized region (e.g., corresponding to some measurement channel(s) of an electronic device and/or the underlying tissue measured by the channel(s)), referred to herein as a spatially localized measurement inconsistency. Such measurement inconsistency may result in an incorrect, low estimate of the physiological characteristic relative to the true characteristic (e.g., an SpO2 estimate may skew lower than the true SpO2). Thus, spatially localized measurement inconsistency can make accurate estimation of SpO2 difficult, especially measurements at certain areas of the body (e.g., at the wrist). As described herein, an algorithm may be used to detect spatially localized measurement inconsistency (e.g., inconsistency above a threshold) and to mitigate or reduce its effect to improve the accuracy of the estimate of the physiological characteristic.

Figure 1C:
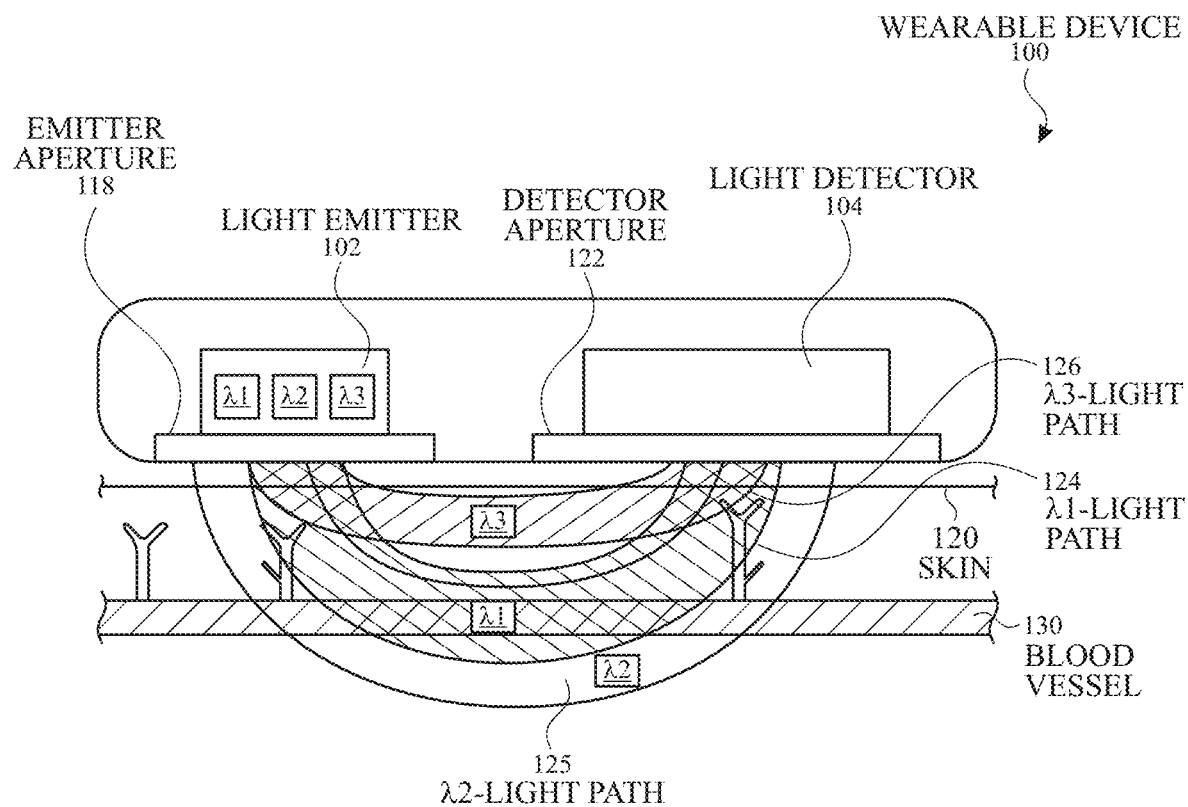
FIG. 1C illustrates a cross-sectional view of exemplary wearable device including one or more light emitters and one or more light detectors according to examples of the disclosure.
Figure 1B:
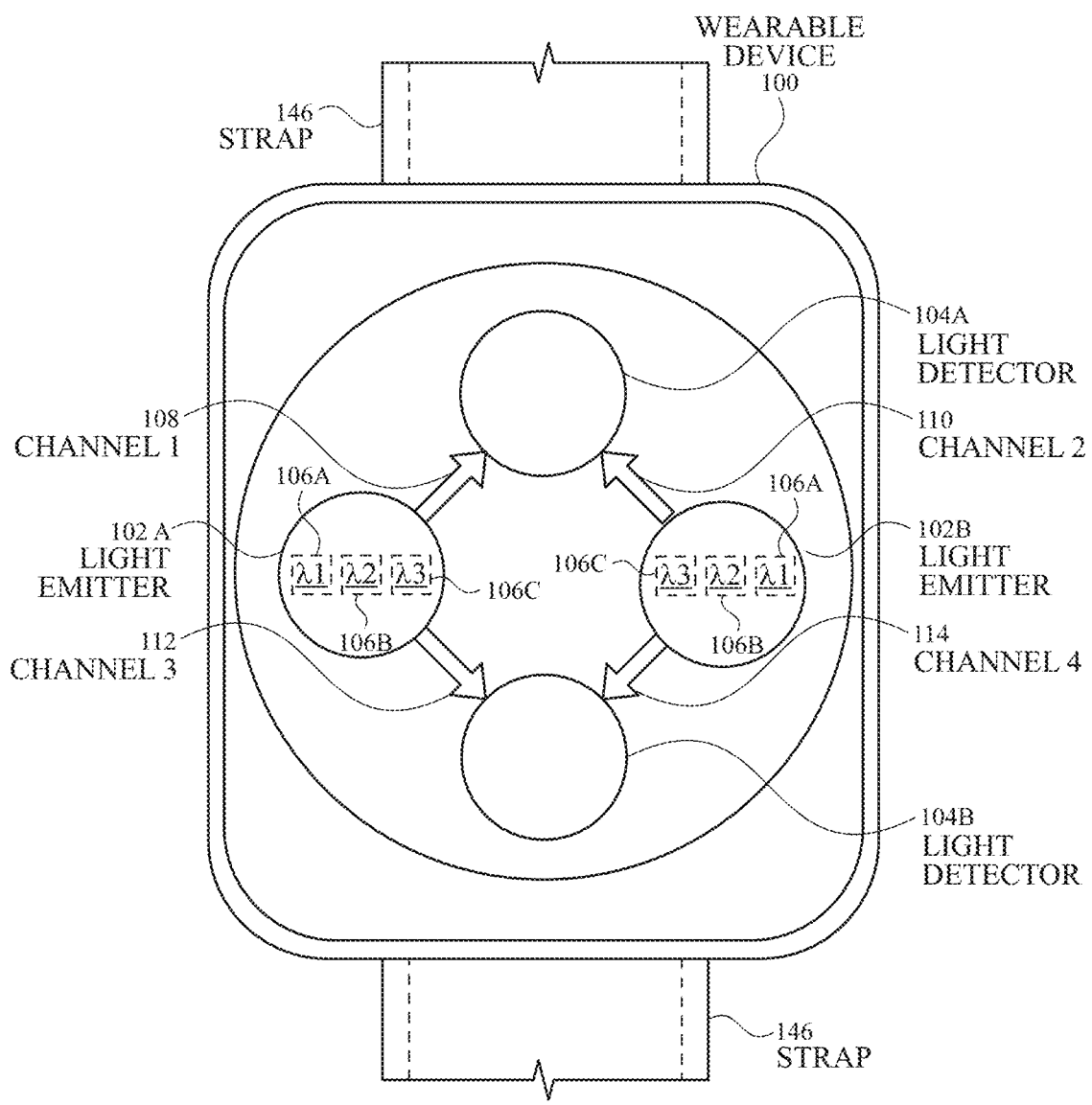

FIGS. 1A-1B illustrate views of an exemplary electronic device including one or more optical sensors according to examples of the disclosure. FIG. 1A illustrates a top view of an exemplary wearable device 100 that can include a touch screen 128 and can be attached to a user using a strap 146 or other fastener. FIG. 1B illustrates a bottom view (underside) of exemplary wearable device 100 including one or more optical sensors comprising one or more light emitters and one or more light detectors according to examples of the disclosure. For example, FIG. 1B illustrates device 100 that can include light emitters 102A-102B and light detectors 104A-104B. Device 100 can be positioned such that light emitters 102A-102B and light detectors 104A-104B are proximate to a user's skin or any other tissue site. For example, device 100 can be held in the user's hand or strapped to the user's wrist, among other possibilities. In some examples, light emitters 102A-102B and light detectors 104A-104B can be in close proximity (e.g., within a threshold distance, such as 5 mm, for example) to the surface of user's skin or can be physically contacting a surface of user's skin, which can reduce the amount of detected light that has not traveled through tissue.

As described herein, each light emitter represents a unique location on the device at which light can be emitted from device, and each light detector represents a unique location on the device at which the device can collect light. The light emitters and light detectors can preferably be optically isolated within the device such that emitted light from an emitter exits the device before being sensed by a detector. As described herein, light emitters can be configured to emit light at a plurality of wavelengths (e.g., at least two wavelengths for SpO2 measurements).

In some examples, each of light emitters 102A-102B can include one or more light emitting components to generate light at different wavelengths. For example, FIG. 1B illustrates each light emitter 102A-102B including three discrete light emitting components 106A-106C (e.g., light emitting diodes (LEDs) or organic light emitting diodes (OLEDs)) configured to generate light at multiple wavelengths including at least wavelengths $\lambda 1$, $\lambda 2$, and $\lambda 3$, respectively. Although three wavelengths are shown, in some examples, device 100 may include light emitting components at fewer or more wavelengths. Additionally, in some examples, each light emitter can include one light emitting component with a tunable wavelength (e.g., voltage or current controlled) or with different filters, rather than using a different light emitting component for each wavelength. In some examples, each light emitter 102A-102B can be optically coupled to each light detector 104A-104B for each wavelength. For example, light emitter 102A can be optically coupled to both light detectors 104A-104B and light emitter 102B can be optically coupled to both light detectors 104A-104B. Light emitter 102A can be configured to emit light (at one or more wavelengths) detected by light detector 104A and detected by light detector 104B. Light emitter 102B can also be configured to emit light (at one or more wavelengths) detected by light detector 104A and detected by light detector 104B. As illustrated in FIG. 1B, a first channel 108 can be used to measure signal at light detector 104A from light emitter 102A (at each respective wavelength), a second channel 110 can be used to measure signal at light detector 104A from light emitter 102B (at each respective wavelength), a third channel 112 can be used to measure signal at light detector 104B from light emitter 102A (at each respective wavelength), and a fourth channel 114 can be used to measure signal at light detector 104B from light emitter 102B (at each respective wavelength). The measured signal at each detector can include light measured from various light paths (e.g., expected distributions of possible light paths through the skin and/or air) between the respective emitter and detector of the channel.

Device 100 can also include processing circuitry to process light detected from light detectors 104A-104B. In some examples, the processing circuitry can be used to determine the user's physiological signals and extract information (e.g., one or more characteristics) from the physiological signals. In some examples, a physiological characteristic can be one or more measures of heart rate or a hemoglobin oxygen saturation level (e.g., an arterial oxygen saturation (SpO2)). In some examples, the processing circuitry can remove or reduce motion artifacts from the physiological signals to account for non-cardiac-induced pulsatile blood volume changes. In some examples, the processing circuitry can process light detected from light detectors 104A-104B for functions independent from determining the user's physiological signals.

FIG. 1C illustrates a cross-sectional view of exemplary wearable device 100 including one or more light emitters and one or more light detectors according to examples of the disclosure. As illustrated in FIG. 1C, light emitter 102 can generate light at one or more wavelengths that can exit device 100 at emitter aperture 118 (e.g., a window). The light can be directed towards, and incident upon, the user's skin 120 and some of the light can be returned back toward device 100 (e.g., reflected and/or scattered from interacting with the skin). The light can reenter device through detector aperture 122 (e.g., a window) and be detected by light detector 104. A portion of light can be absorbed by molecules in skin 120, vasculature, and/or blood. Pulsatile blood flow in the user can lead to changes in the arterial vessel diameters, tissue hemoglobin concentration or volume, red blood cell orientation, velocity, or other physical states during a pressure change (e.g., diastole to systole), which can be included in light (e.g., via a scattering or absorption contrast mechanism) within the field of view of light detector 104. In some examples, heart rate can be estimated based on the changes in the detected light at one or more wavelengths due to pulsatile blood flow. In some examples, oxygen saturation in the blood can be estimated based on a ratio between physiological signal measurements (e.g., light intensity signals at light detectors) at two (or more) wavelengths. For example, oxygen saturation can be estimated based on a relative modulation ratio at two or more wavelengths. In some examples, the modulation ratio can be a perfusion index (PI) ratio based on physiological signal measurements at two or more wavelengths. Although the intensity of the physiological signal (or more generally the magnitude of each independent wavelength measurement) may change due to variations in the pulsations of blood, movement and the heterogeneity of tissue, the relative modulation ratio (e.g., between red light and infrared light) can be relatively stable indicator of oxygen saturation (e.g., via an empirical mapping between the relative modulation ratio and oxygen saturation).

In some examples, the signals from the one or more light emitters and one or more light detectors can be utilized to perform other functions aside from measuring the user's physiological signals and extracting information/characteristics from the physiological signals. For example, one or more light emitters and one or more light detectors can be configured for monitoring whether or not the device remains in contact with a user's skin (e.g., on-wrist and/or off-wrist detection) and/or whether the device is in contact with a non-skin surface such as a table.

FIG. 1C illustrates exemplary light paths for three different wavelengths $\lambda 1$, $\lambda 2$ and $\lambda 3$. Light path 124 can correspond to expected distributions of possible light paths at wavelength 21 (e.g., in the wavelength range of 620 nm-750 nm) and light path 125 can correspond to expected distributions of possible light paths at wavelength $\lambda 2$ (e.g., in the wavelength range of 750 nm-1400 nm). In some examples, wavelength $\lambda 1$ can be in the range of visible light (e.g., 400 nm-700 nm) and wavelength $\lambda 2$ can be in the range of near-infrared (NIR) light (e.g., 700-1100 nm), which can be strongly absorbed by blood and other molecules in the user's tissue and blood. In some examples, wavelength $\lambda 1$ can be red light and wavelength $\lambda 2$ can be IR light. Light path 126 can correspond to expected distributions of possible light paths at wavelength $\lambda 3$ (e.g., in the wavelength range of 495 nm-570 nm). In some examples, $\lambda 3$ can be in a lower wavelength range of visible light (e.g., 400 nm-495 nm), such as blue light, or near ultraviolet light (e.g., 300 nm-400 nm), or other portions of the visible light, NIR, short-wave IR spectra. It should be understood that these wavelength ranges are for exemplary purposes and different wavelength ranges are possible for $\lambda 1$, $\lambda 2$, and $\lambda 3$ (or any additional wavelengths). In some examples, the light at multiple wavelengths from the multiple light emitting components of an emitter exiting the device can preferably partially or fully overlap (e.g., light paths 124-126 can be partially or fully overlapping). As shown in FIG. 1C, in some examples, different wavelengths can penetrate different depths within skin 120. For example, light paths 124 and 125 corresponding to wavelengths $\lambda 1$ and $\lambda 2$ can penetrate more deeply within the skin 120 and underlying tissue, whereas light path 126 corresponding to wavelength $\lambda 3$ can penetrate less deeply within skin 120 and the underlying tissue. Additionally, although the light paths may penetrate different depths, it is understood that light at some wavelengths can penetrate a variety of depths including shallower and deeper within the tissue.

Skin 120 and underlying tissue can include the blood vessels (arterial and venous) such as blood vessel 130. Light emitter 102 and light sensor 104 can be located and wavelengths can be selected such that light paths 124 and 125 corresponding to wavelengths $\lambda 1$ and $\lambda 2$ can be sensitive to arterial blood volume changes to enable an estimation of the characteristic of a user's physiological signals.

Figure 1D:
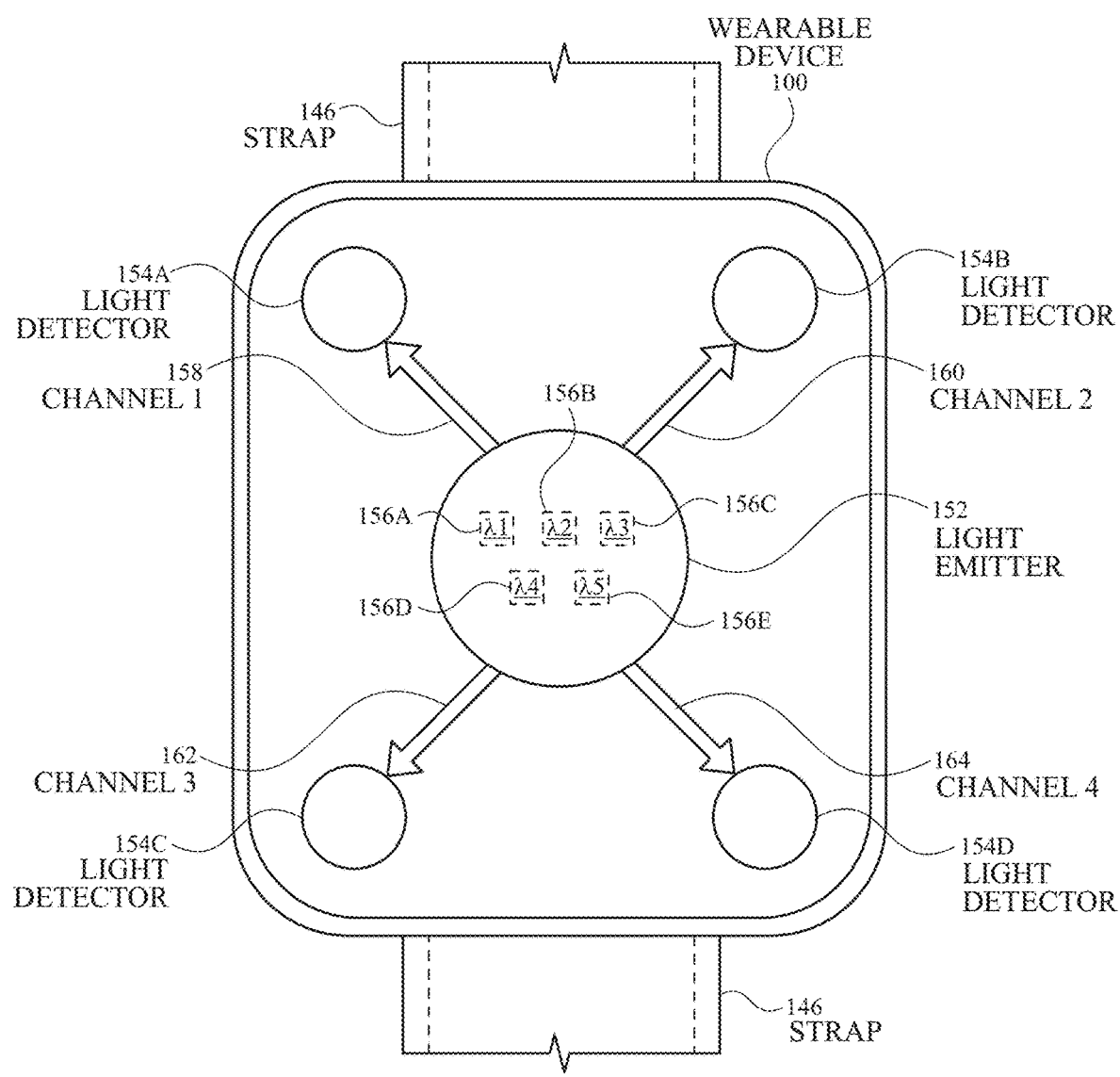
FIGS. 1D-1E illustrate alternative arrangements of light emitters and light detectors on the underside of an exemplary electronic device according to examples of the disclosure.
Figure 1E:
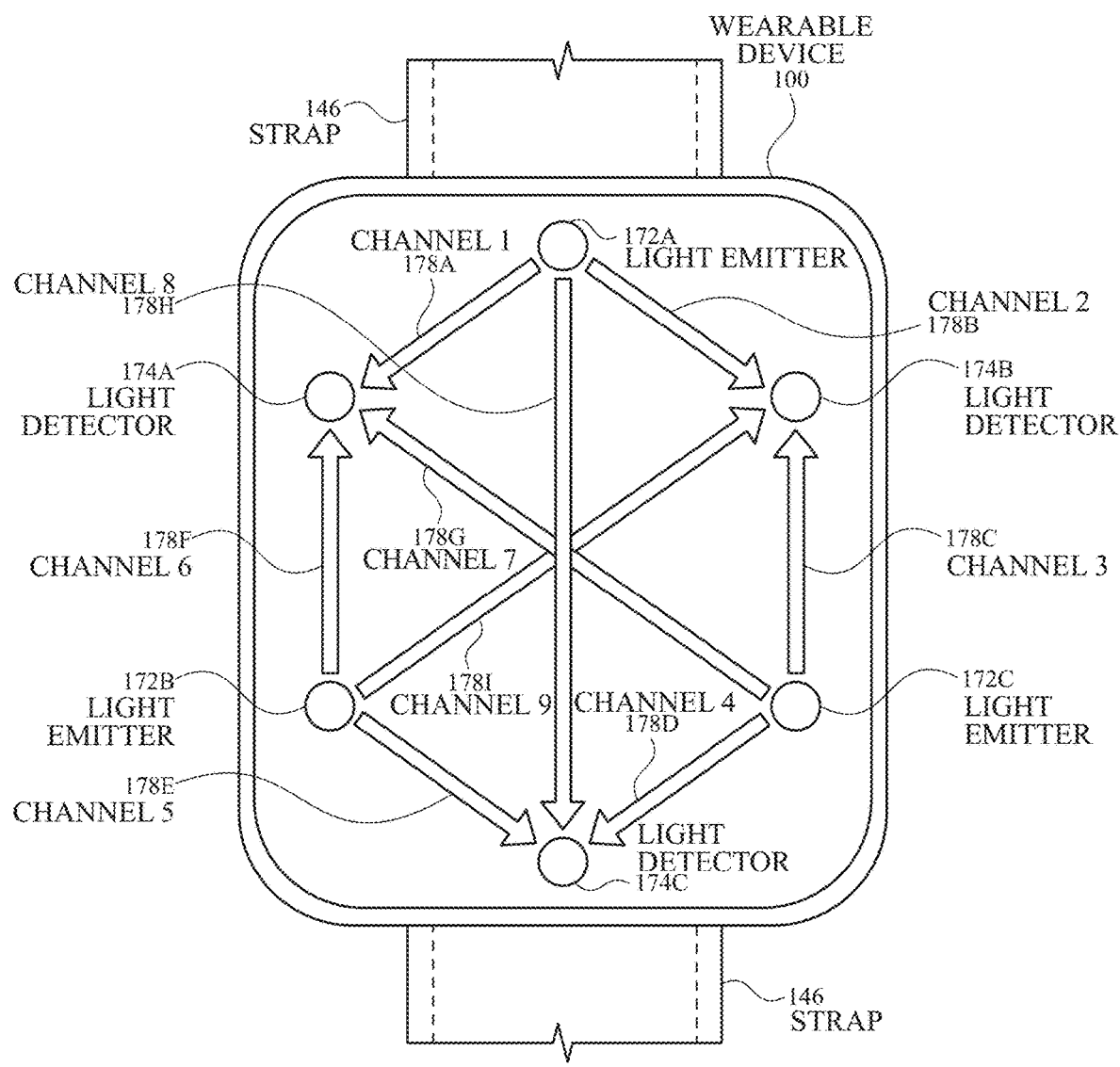

FIGS. 1D-1E illustrate alternative arrangements of light emitters and light detectors on the underside of an exemplary electronic device according to examples of the disclosure. FIG. 1D illustrates device 100 that can include light emitter 152 in a center of the device and light detectors 154A-154D. Light emitter 152 can include one or more light emitting components to generate light at different wavelengths. For example, FIG. 1D illustrates light emitter 152 including five light emitting components 156A-E (e.g., LEDs or OLEDs) configured to generate light at wavelengths $\lambda 1$, $\lambda 2$, $\lambda 3$, $\lambda 4$ and $\lambda 5$, respectively. Although five wavelengths are shown, in some examples, device 100 may include light emitting components at fewer or more wavelengths (or one tunable/filterable light source) or may include different types of light emitting components (e.g., laser diodes). Light emitter 152 can be optically coupled to one or more (or each of) light detectors 154A-154D for one or more (or each of the) wavelengths. In some examples, light emitter 152 can be configured to emit light (at one or more wavelengths) detected by light detector 154A, detected by light detector 154B, detected by light detector 154C and detected by light detector 154D. As illustrated in FIG. 1D, a first channel 158 can be used to measure signal at light detector 154A from light emitter 152 (e.g., at each respective wavelength), a second channel 160 can be used to measure signal at light detector 154B from light emitter 152 (at each respective wavelength), a third channel 162 can be used to measure signal at light detector 154C from light emitter 152 (at each respective wavelength), and a fourth channel 164 can be used to measure signal at light detector 154D from light emitter 152 (at each respective wavelength). The measured signal at each detector (at each respective wavelength) can include light that has traversed various light paths (e.g., expected distributions of possible light paths through the skin and/or air) between the respective emitter and detector of the channel.

Although FIGS. 1B and 1D illustrate four channels (each operable for emitting/detecting light at multiple wavelengths), in some examples, fewer or additional channels may be implemented. For example, a single channel including one light emitter and one light detector can be used. In some examples, additional light emitters and/or light detectors may be used to form additional channels. For example, adding one or more additional light detectors to the configurations in FIG. 1B or 1D can increase the number of channels.

FIG. 1E illustrates device 100 that can include multiple light emitters 172A-172C and multiple light detectors 174A-174C arranged in a pattern around the perimeter of the device. Although the three emitters and detectors are shown in a hexagonal arrangement with an alternating pattern of emitters/detectors, it is understood that other arrangements are possible with different shaped arrangements (e.g., circle, polygon, etc.), non-alternating arrangements, and/or using more or fewer light emitters and light detectors. Light emitter 172A-172C can include one or more light emitting components (not shown) to generate light at different wavelengths (e.g., λ1, λ2, λ3, etc.). Light emitters 172A-172C can be optically coupled to one or more (or each of) light detectors 174A-174C for one or more (or each of the) wavelengths. In some examples, light emitter 172A can be configured to emit light (at one or more wavelengths) detected by light detector 174A, detected by light detector 174B, and detected by light detector 174C. As illustrated in FIG. 1E, a first channel 178A can be used to measure signal at light detector 174A from light emitter 172A (e.g., at each respective wavelength), a second channel 178B can be used to measure signal at light detector 174B from light emitter 172A (at each respective wavelength), and a third channel 178H can be used to measure signal at light detector 174C from light emitter 172A (at each respective wavelength). In a similar manner, a fourth channel 178F can be used to measure signal at light detector 174A from light emitter 172B (e.g., at each respective wavelength), a fifth channel 178I can be used to measure signal at light detector 174B from light emitter 172B (at each respective wavelength), a sixth channel 178E can be used to measure signal at light detector 174C from light emitter 172B (at each respective wavelength), a seventh channel 178G can be used to measure signal at light detector 174A from light emitter 172C (e.g., at each respective wavelength), an eighth channel 178C can be used to measure signal at light detector 174B from light emitter 172C (at each respective wavelength), and a ninth channel 178D can be used to measure signal at light detector 174C from light emitter 172C (at each respective wavelength). The measured signal at each detector (at each respective wavelength) can include light that has traversed various light paths (e.g., expected distributions of possible light paths through the skin and/or air) between the respective emitter and detector of the channel.

It is understood that the light detectors of device 100 (e.g., light detector(s) 104, 104A-104B, 154A-154D, and 174A-174C) can, in some examples, include a single light detection component (e.g., photodiode or other suitable photodetector). In some examples, some or all of the light detectors of device 100 can include multiple light detection components (e.g., an array of photodiodes). Using multiple light detection components per light detector can allow for greater granularity in signal processing. Additionally or alternatively, the multiple light components can be used with different optical filters to provide simultaneous measurements for multiple wavelengths (e.g., each light detection component can include a different filter to enable measurement of a different wavelength of light).

Figure 2:
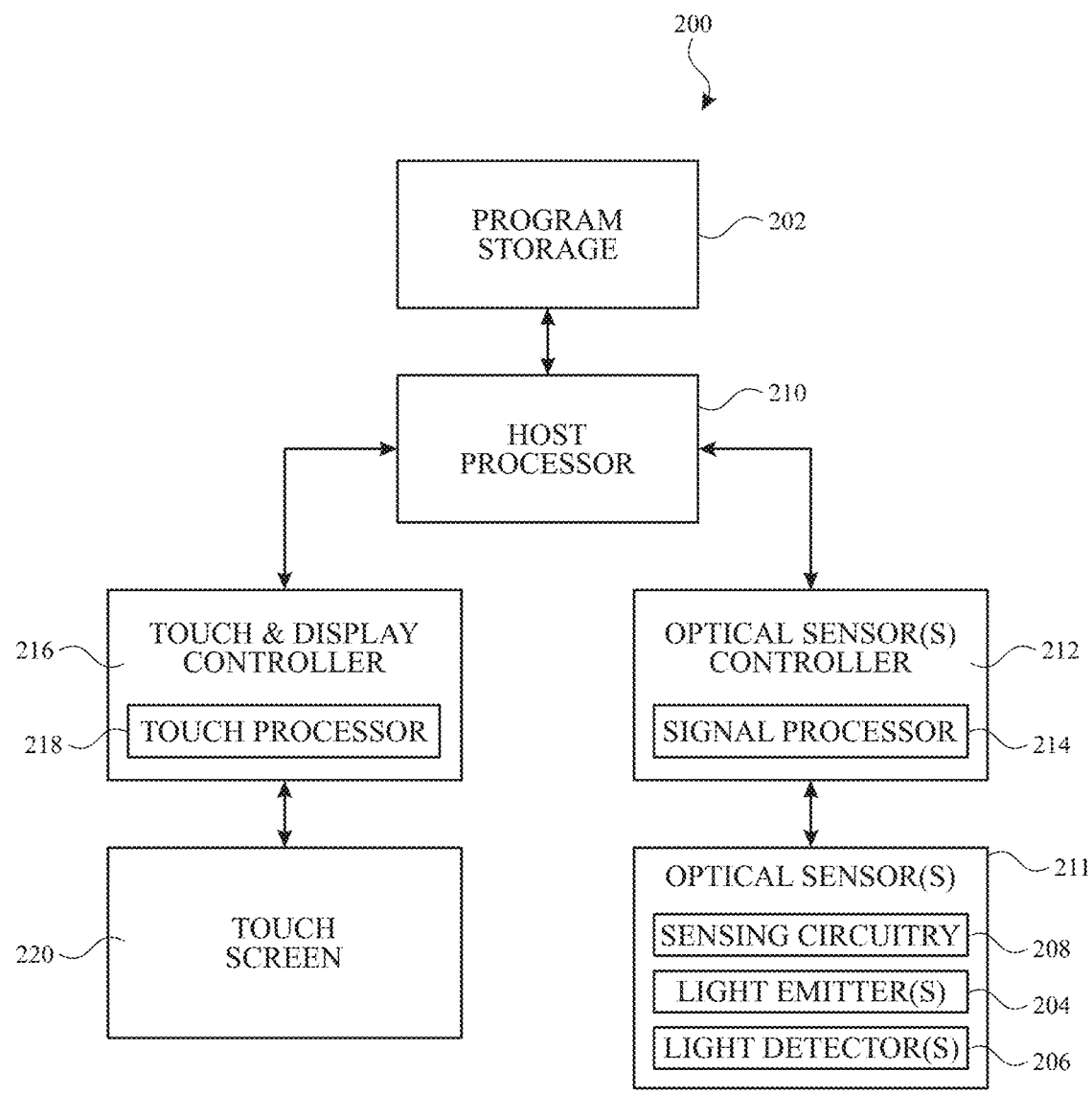
FIG. 2 illustrates an exemplary block diagram of a computing system including an optical sensor according to examples of the disclosure.

FIG. 2 illustrates an exemplary block diagram of a computing system including an optical sensor according to examples of the disclosure. Although primarily described herein as a wearable device, the computing system may alternatively be implemented partially or fully in a non-wearable device. For example, the sensors and/or processing described herein can be implemented partially or fully in a mobile telephone, media player, tablet computer, personal computer, server, etc. In some examples, the light emitters and light detectors can be implemented in a wearable device (e.g., a wristwatch) and the processing of the data can be performed in a non-wearable device (e.g., a mobile phone). Processing and/or storage of the physiological signals in a separate device can enable the device including the physiological sensors (e.g., a wristwatch) to be space and power efficient (which can be important features for portable/wearable devices).

Computing system 200 can correspond to device 100 illustrated in FIGS. 1A-1E (or may be implemented in other wearable or non-wearable electronic devices). Computing system 200 can include a processor 210 (or more than one processor) programmed to (configured to) execute instructions and to carry out operations associated with computing system 200. For example, using instructions retrieved from program storage 202, processor 210 can control the reception and manipulation of input and output data between components of computing system 200. Processor 210 can be a single-chip processor (e.g., an application specific integrated circuit) or can be implemented with multiple components/circuits.

In some examples, processor 210 together with an operating system can operate to execute computer code, and produce and/or use data. The computer code and data can reside within a program storage 202 that can be operatively coupled to processor 210. Program storage 202 can generally provide a place to hold data that is being used by computing system 200. Program storage block 202 can be any non-transitory computer-readable storage medium, and can store, for example, history and/or pattern data relating to PPG signals and relative modulation ratio (e.g., perfusion index ratio) values measured by a configuration of light emitter(s) 204 and light detector(s) 206 (e.g., as illustrated in FIG. 1B, 1D or 1E). By way of example, program storage 202 can include Read-Only Memory (ROM), Random-Access Memory (RAM), hard disk drive and/or the like. The computer code and data could also reside on a removable storage medium and loaded or installed onto computing system 200 when needed. Removable storage mediums include, for example, CD-ROM, DVD-ROM, Universal Serial Bus (USB), Secure Digital (SD), Compact Flash (CF), Memory Stick, Multi-Media Card (MMC) and/or a network component.

Computing system 200 can also include one or more input/output (I/O) controllers that can be operatively coupled to processor 210. I/O controllers can be configured to control interactions with one or more I/O devices (e.g., touch sensor panels, display screens, touch screens, physical buttons, dials, slider switches, joysticks, or keyboards). I/O controllers can operate by exchanging data between processor 210 and the I/O devices that desire to communicate with processor 210. The I/O devices and I/O controller can communicate through a data link. The data link can be a unidirectional or bidirectional link. In some cases, I/O devices can be connected to I/O controllers through wireless connections. A data link can, for example, correspond any wired or wireless connection including, but not limited to, PS/2, Universal Serial Bus (USB), Firewire, Thunderbolt, Wireless Direct, IR, RF, Wi-Fi, Bluetooth or the like.

For example, computing system 200 can include an optical sensor controller 212 operatively coupled to processor 210 and to one or more optical sensors 211. The optical sensor(s) can include light emitter(s) 204, light detector(s) 206 and corresponding sensing circuitry 208 (e.g., analog circuitry to drive emitters and measure signals at the detector, provide processing (e.g., amplification, filtering), and convert analog signals to digital signals). As described herein, light emitters 204 and light detectors 206 can be configured to generate and emit light into a user's skin and detect returning light (e.g., reflected and/or scattered) to measure a physiological signal (e.g., a PPG signal). The absorption and/or return of light at different wavelengths can also be used to determine a characteristic of the user (e.g., oxygen saturation, heart rate) and/or about the contact condition between the light emitters 204/light detectors 206 and the user's skin. Measured raw data from the light emitters 204, light detectors 206 and sensing circuitry 208 can be transferred to processor 210, and processor 210 can perform the signal processing described herein to estimate a characteristic (e.g., oxygen saturation, heart rate, etc.) of the user from the physiological signals. Processor 210 and/or optical sensor controller 212 can operate light emitters 204, light detectors 206 and/or sensing circuitry 208 to measure data from the optical sensor. In some examples, optical sensor controller 212 can include timing generation for light emitters 204, light detectors 206 and/or sensing circuitry 208 to sample, filter and/or convert (from analog to digital) signals measured from light at different wavelengths. Optical sensor controller 212 can process the data in signal processor 214 and report outputs (e.g., PPG signal, relative modulation ratio, perfusion index, heart rate, on-wrist/off-wrist state, etc.) to the processor 210. Signal processor 214 can be a digital signal processing circuit such as a digital signal processor (DSP). The analog data measured by the optical sensor(s) 211 can be converted into digital data by an analog to digital converter (ADC), and the digital data from the physiological signals can be stored for processing in a buffer (e.g., a FIFO) or other volatile or non-volatile memory (not shown) in optical sensor controller 212. In some examples, some light emitters and/or light detectors can be activated, while other light emitters and/or light detectors can be deactivated to conserve power, for example, or for time-multiplexing (e.g., to avoid interference between channels). In some examples, processor 210 and/or optical sensor controller 212 can store the raw data and/or processed information in memory (e.g., ROM or RAM) for historical tracking or for future diagnostic purposes. Additional detail regarding optical sensors and processing optical signals is described below.

Computing system 200 can also include, in some examples, a touch and display controller 216 operatively coupled to processor 210 and to touch screen 220. Touch screen 220 can be configured to display visual output in a graphical user interface (GUI), for example. The visual output can include text, graphics, video, and any combination thereof. In some examples, the visual output can include a text or graphical representation of the physiological signal (e.g., a PPG waveform) or a characteristic of the physiological signal (e.g., oxygen saturation, heart rate, etc.) Touch screen can be any type of display including a liquid crystal display (LCD), a light emitting polymer display (LPD), an electroluminescent display (ELD), a field emission display (FED), a light emitting diode (LED) display, an organic light emitting diode (OLED) display, or the like. Processor 210 can send raw display data to touch and display controller 216, and touch and display controller 216 can send signals to touch screen 220. Data can include voltage levels for a plurality of display pixels in touch screen 220 to project an image. In some examples, processor 210 can be configured to process the raw data and send the signals to touch screen 220 directly. Touch and display controller 216 can also detect and track touches or near touches (and any movement or release of the touch) on touch screen 220. For example, touch processor 218 can process data representative of touch or near touches on touch screen 220 (e.g., location and magnitude) and identify touch or proximity gestures (e.g., tap, double tap, swipe, pinch, reverse-pinch, etc.). Processor 210 can convert the detected touch input/gestures into interaction with graphical objects, such as one or more user-interface objects, displayed on touch screen 220 or perform other functions (e.g., to initiate a wake of the device or power on one or more components).

In some examples, touch and display controller 216 can be configured to send raw touch data to processor 210, and processor 210 can process the raw touch data. In some examples, touch and display controller 216 can process raw touch data itself (e.g., in touch processor 218). The processed touch data (touch input) can be transferred from touch processor 218 to processor 210 to perform the function corresponding to the touch input. In some examples, a separate touch sensor panel and display screen can be used, rather than a touch screen, with corresponding touch controller and display controller.

In some examples, the touch sensing of touch screen 220 can be provided by capacitive touch sensing circuitry (e.g., based on mutual capacitance and/or self-capacitance). For example, touch screen 220 can include touch electrodes arranged as a matrix of small, individual plates of conductive material or as drive lines and sense lines, or in another pattern. The electrodes can be formed from a transparent conductive medium such as ITO or ATO, although other partially or fully transparent and non-transparent materials (e.g., copper) can also be used. In some examples, the electrodes can be formed from other materials including conductive polymers, metal mesh, graphene, nanowires (e.g., silver nanowires) or nanotubes (e.g., carbon nanotubes). The electrodes can be configurable for mutual capacitance or self-capacitance sensing or a combination of mutual and self-capacitance sensing. For example, in one mode of operation, electrodes can be configured to sense mutual capacitance between electrodes; in a different mode of operation, electrodes can be configured to sense self-capacitance of electrodes. During self-capacitance operation, a touch electrode can be stimulated with an AC waveform, and the self-capacitance to ground of the touch electrode can be measured. As an object approaches the touch electrode, the self-capacitance to ground of the touch electrode can change (e.g., increase). This change in the self-capacitance of the touch electrode can be detected and measured by the touch sensing system to determine the positions of one or more objects when they touch, or come in proximity to without touching, the touch screen. During mutual capacitance operation, a first touch electrode can be stimulated with an AC waveform, and the mutual capacitance between the first touch electrode and a second touch electrode can be measured. As an object approaches the overlapping or adjacent region of the first and second touch electrodes, the mutual capacitance therebetween can change (e.g., decrease). This change in the mutual capacitance can be detected and measured by the touch sensing system to determine the positions of one or more objects when they touch, or come in proximity to without touching, the touch screen. In some examples, some of the electrodes can be configured to sense mutual capacitance therebetween and some of the electrodes can be configured to sense self-capacitance thereof.

Note that one or more of the functions described herein, including estimating a physiological characteristic according to examples of the disclosure, can be performed by firmware stored in memory (or in program storage 202) and executed by physiological sensor controller 212, touch and display controller 216 or processor 210. The firmware can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer-readable storage medium" can be any medium (excluding signals) that can contain or store the program for use by or in connection with the instruction execution system, apparatus, or device. The computer-readable storage medium can include, but is not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

The firmware can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium.

Referring back to FIG. 1B, light emitters 102A-102B can generate light and light detectors 104A-104B can measure light at multiple wavelengths (e.g., $\lambda 1$, $\lambda 2$, $\lambda 3$). In some examples, three light emitting components 106A-106C can be co-located (within a threshold distance of one another, e.g., less than 5 mm) in each of light emitters 102A-102B. In some examples, each of the light emitting components can be driven in a time-multiplexed manner. For example, during a measurement period of duration T (from time t0 to t6), a first light emitting component 106A of light emitter 102A can be driven at wavelength $\lambda 1$ and light can be detected at light detectors 104A-104B (from t0 to t1), a second light emitting component 106B of light emitter 102A can be driven at wavelength $\lambda 2$ and light can be detected at light detectors 104A-104B (from t1 to t2), a third light emitting component 106C of light emitter 102A can be driven at wavelength $\lambda 3$ and light can be detected at light detectors 104A-104B (from t2 to t3), a fourth light emitting component 106A of light emitter 102B can be driven at wavelength $\lambda 1$ and light can be detected at light detectors 104A-104B (from t3 to t4), a fifth light emitting component 106B of light emitter 102B can be driven at wavelength $\lambda 2$ and light can be detected at light detectors 104A-104B (from t4 to t5), and a sixth light emitting component 106C of light emitter 102B can be driven at wavelength $\lambda 3$ and light can be detected at light detectors 104A-104B (from t5 to t6). Ideally, the measurement period can be less than a threshold duration. Reducing the duration of measurement period can allow for the measurements at different wavelengths to be as co-located in time as possible. In some examples, the duration of the measurement period can be less than 100 ms. The above measurements can result in a sample for each channel (e.g., four channels of FIG. 1B, 9 channels for FIG. 1E) at each wavelength (e.g., $\lambda 1$, $\lambda 2$, $\lambda 3$) for the measurement period. The sample for each channel can be used to compute physiological characteristics such as perfusion indices, perfusion index ratios, SpO2, etc. In some examples, the light emitting components can be frequency-multiplexed such that multiple light emitting components to concurrently emit light and detectors can differentiate between the light emitting components based on the frequency content.

Figure 3A:
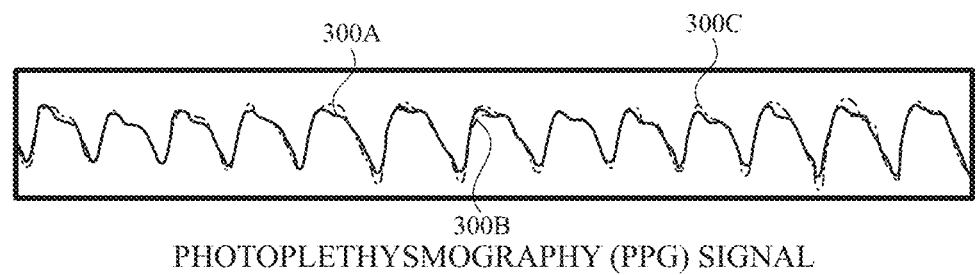
FIGS. 3A-3B illustrate example photoplethysmogram (PPG) signals measured at different wavelengths according to examples of the disclosure.
Figure 3B:
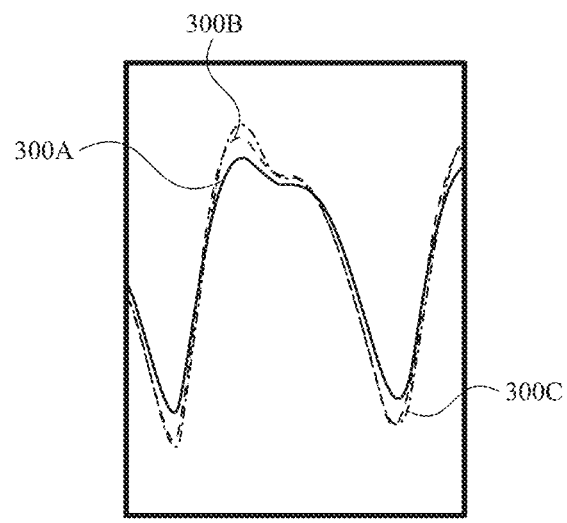

FIGS. 3A-3B illustrate example photoplethysmogram (PPG) signals measured at different wavelengths according to examples of the disclosure. The PPG signals can include cyclical "beats" (or "pulses") corresponding to a heartbeat (e.g., each "beat" or "pulse" indicative of one occurrence of the repeating cardiac cycle). FIGS. 3A-3B illustrate a PPG signal for each of wavelengths $\lambda 1$, $\lambda 2$ and $\lambda 3$ (e.g., while device 100 is properly secured to skin 120 to establish good contact between the optical sensor(s) and the skin). FIG. 3A illustrates PPG signals 300A, 300B, 300C with multiple beats and FIG. 3B illustrates a larger view of an exemplary beat, in which the waveform shapes of PPG signals 300A-300C can be similar and correspond to pulsatile blood information. Although not shown in FIGS. 3A-3B, in some examples, when device is not properly secured to skin 120 (light or poor content), the waveform of PPG signal can be different in shape and/or relative amplitude (and may or may not correspond to pulsatile blood information) for wavelength $\lambda 3$ (e.g., different than the shape and/or relative amplitude of PPG signal 300C, whereas the waveforms of PPG signals 300A and 300B may be similar even with poorer contact between the optical sensor and tissue). As a result, poor contact conditions may result in an inaccurate estimate of the physiological signal characteristic.

In some examples, a sensor can be used to estimate a contact condition. For example, device 100 can include a touch sensor (e.g., capacitive, resistive, ultrasonic, etc.), proximity sensor (e.g., an infrared sensor), force sensor or other suitable sensor separate from optical sensor(s) 211 on the underside of the device to estimate a contact condition between device 100 can the user's tissue. In some examples, one or more channels of optical sensor 211 can be used to estimate the contact condition. In some examples, measurements at wavelength $\lambda 3$ (e.g., green light, blue light, etc.) can be used to estimate the contact condition (or more generally contribute to quality metrics) and identify which channels include measurements at wavelengths $\lambda 1$ and $\lambda 2$ (e.g., red light and IR light) that may be suitable for physiological signal processing and/or how to process the measurements at wavelengths $\lambda 1$ and $\lambda 2$ in the physiological signal processing. In some examples, when poor contact conditions are estimated based on wavelengths $\lambda 3$ (e.g., when the device is outside a threshold distance from the surface of the user's skin or in poor contact) or based on another sensor (e.g., touch, proximity, force, etc.), the device can forgo estimating or reporting an estimated physiological characteristic based on wavelengths λ1 and λ2 (e.g., per channel or for all channels of the device). Although beats are shown, it is understood that the methods described herein can be applied based on instantaneous measurements, on a beat-by-beat basis, on an average of multiple beats, or after converting to a different domain, such as a frequency domain (e.g., using a Fourier transform) or wavelet domain.

As described above, other conditions aside from contact condition may result in an inaccurate estimate of the physiological signal characteristic. For example, while device 100 is at an unexpected orientation relative to skin 120 or in the presence of transient or permanent tissue variations, measurements at wavelengths λ1 and λ2 (PPG signals) may result in inaccurate measurement of the physiological signal characteristic, despite the PPG signals having quality characteristics consistent with physiologically valid PPG signals showing a consistent cardiac signal indicative of accurate measurements of the physiological signal characteristic. In particular, the presence of a spatially localized measurement inconsistency may result in an incorrect, low estimate of the physiological signal characteristic relative to the true characteristic (e.g., SpO2 estimate may skew lower than the true SpO2). As described herein, a measurement inconsistency mitigation algorithm may be used to detect spatially localized measurement inconsistency and to mitigate or reduce its effect to improve the accuracy of the estimated physiological signal characteristic. In some examples, when the spatially localized measurement inconsistency is detected, the device can forgo estimating or reporting an estimated physiological characteristic (e.g., under the assumption that the measurement may be inaccurate).

Figure 4A:
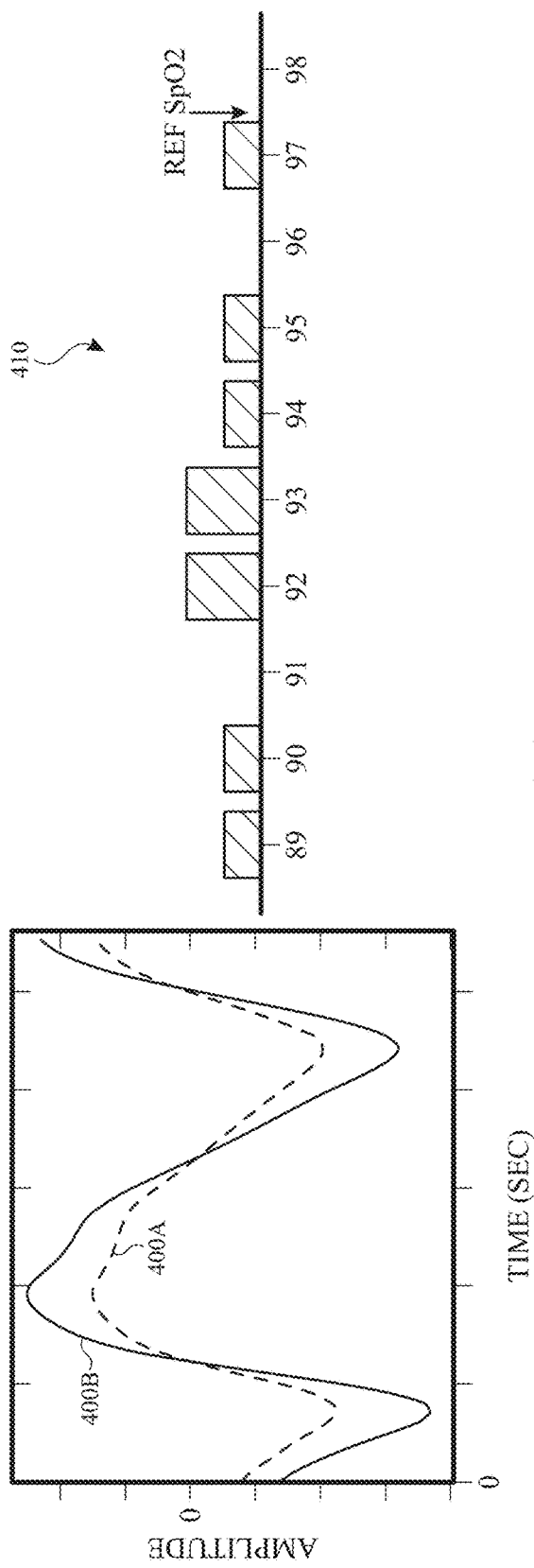
FIGS. 4A and 4B illustrate example histograms and corresponding example PPG signals measured at different wavelengths according to examples of the disclosure.
Figure 4B:
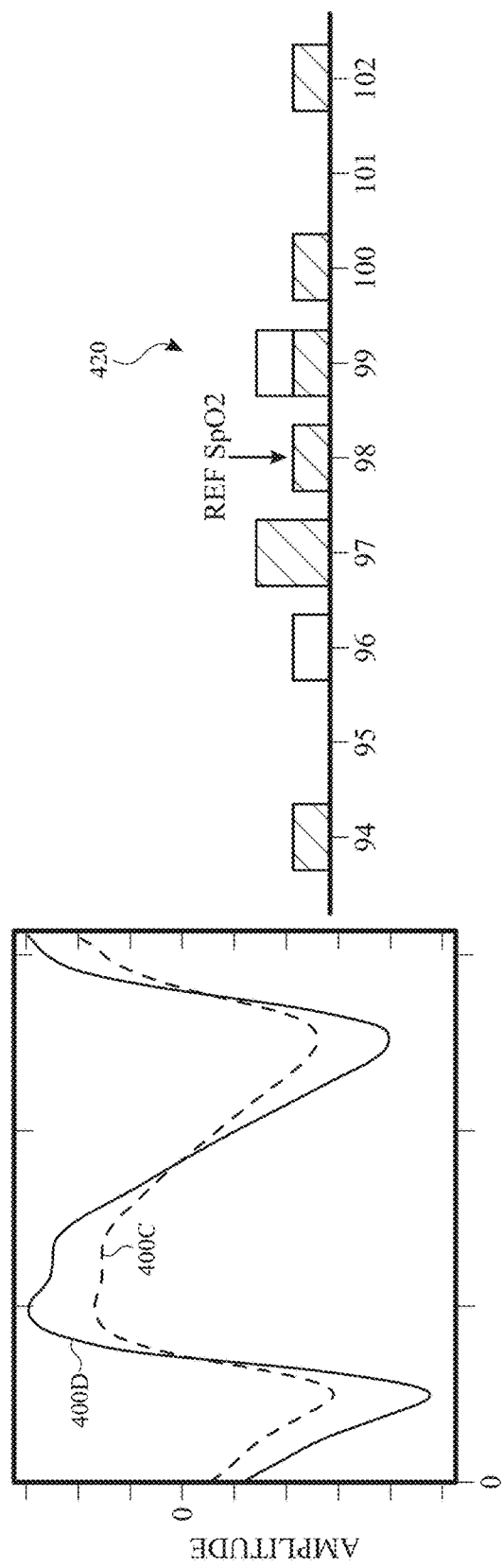

FIGS. 4A and 4B illustrate example histograms and corresponding example PPG signals measured at different wavelengths according to examples of the disclosure. FIG. 4A corresponds to an example case with a spatially localized measurement inconsistency that results in an incorrect estimated SpO2 (e.g., outside of a threshold of the reference SpO2), and FIG. 4B corresponds to an example case without a spatially localized measurement inconsistency where the SpO2 is correctly estimated (e.g., within a threshold of the reference SpO2). Histograms 410 and 420 illustrate estimated per-channel values ("cSpO2" values, where c refers to channel) from measurements of multiple channels (e.g., one cSpO2 estimate per channel for the nine channels in the configuration of FIG. 1E). In some examples, the multiple cSpO2 values from measurements of the multiple channels can be combined to estimate a SpO2 value for the user. In some examples, an average of the multiple cSpO2 values can be used to compute the estimated SpO2 value for the user. In some examples, other combinations are possible including a weighted average, in which the multiple cSpO2 values are weighted according to signal quality metrics (e.g., imaging weights described herein) for the multiple channels. In some examples, the weighted average gives no weight to those channels with poor signal quality metrics (e.g., indicated without shading in histogram 420) and giving full weight to those channels with good signal quality metrics (e.g., indicated with shading in histograms 410, 420). For example, histogram 410 can produce a composite average SpO2 value of 92.8% and histogram 420 can produce composite average SpO2 value of 98%. Histograms 410 and 420 also indicate a reference SpO2 value of a user (e.g., the SpO2 reference can be measured by another pulse oximeter, blood draw, etc.), as represented by the reference SpO2 ("REF SpO2"). FIG. 4A corresponds to a user with an SpO2 value of approximately 97.4% and FIG. 4B corresponds to a user with an SpO2 value of approximately 98%. As shown in FIGS. 4A-4B, the spatially localized measurement inconsistency can result in the estimated SpO2 being 5%+ off from the reference SpO2 (skewing lower than the true SpO2 value), whereas without the spatially localized measurement inconsistency, the estimated SpO2 is within 0.5% from the reference SpO2.

In some examples, the accuracy of the SpO2 measurement may be improved by detecting and mitigating this spatially localized measurement inconsistency to avoid estimation and reporting of an incorrect physiological characteristic to the user. However, as shown in FIGS. 4A-4B, example PPG signals 400A-400B at wavelengths λ1 and λ2 for a respective channel in the presence of a spatially localized measurement inconsistency may be difficult to distinguish from example PPG signals 400C-400D at wavelengths λ1 and λ2 for a respective channel without the presence of a spatially localized measurement inconsistency. In both instances, for example, the pairs of PPG waveforms 400A-400B and 400C-400D appear similar and exhibit signal quality consistent with physiologically valid PPG signals showing a consistent cardiac signal. Such signal quality is often indicative of accurate measurements of the physiological signal characteristic, but that may not be the case in the presence of the spatially localized measurement inconsistency.

In some examples, the absence of a spatially localized measurement inconsistency may be detected from information about the cSpO2 values from multiple channels. For example, in the presence of a spatially localized measurement inconsistency, the cSpO2 measurement skew lower than the reference SpO2 (and particularly for channels that probe deeper into tissue). Therefore, identifying relatively high (e.g., above a threshold) readings of cSpO2 (and/or seeing consistent behavior across channels that probe different depths into tissue), the pulse oximetry system can exclude the possibility of a spatially localized measurement inconsistency (e.g., because it does not exist or does not meaningfully affect the estimated SpO2 measurement if it does exist). For example, histogram 420 corresponds to a relatively high reading of estimated SpO2 (97.7%), which is unlikely in the presence of a spatially localized measurement inconsistency, whereas histogram 410 corresponds to an SpO2 reading (92%) that may be indicative of a spatially localized measurement inconsistency skewing the reading lower or a true SpO2 reading (or may be an accurate SpO2 reading of a person with lower SpO2). In some examples, when the absence of a spatially localized measurement inconsistency is not detected (e.g., because a spatially localized measurement inconsistency exists or cannot yet be excluded), then the estimated SpO2 reading can be ignored and not reported to the user. In some examples, when the absence of a spatially localized measurement inconsistency is not detected (e.g., because a spatially localized measurement inconsistency exists or cannot yet be excluded), then a measurement inconsistency mitigation algorithm is used to estimate the SpO2 reading and mitigate any potential spatially localized measurement inconsistency.

Figure 5A:
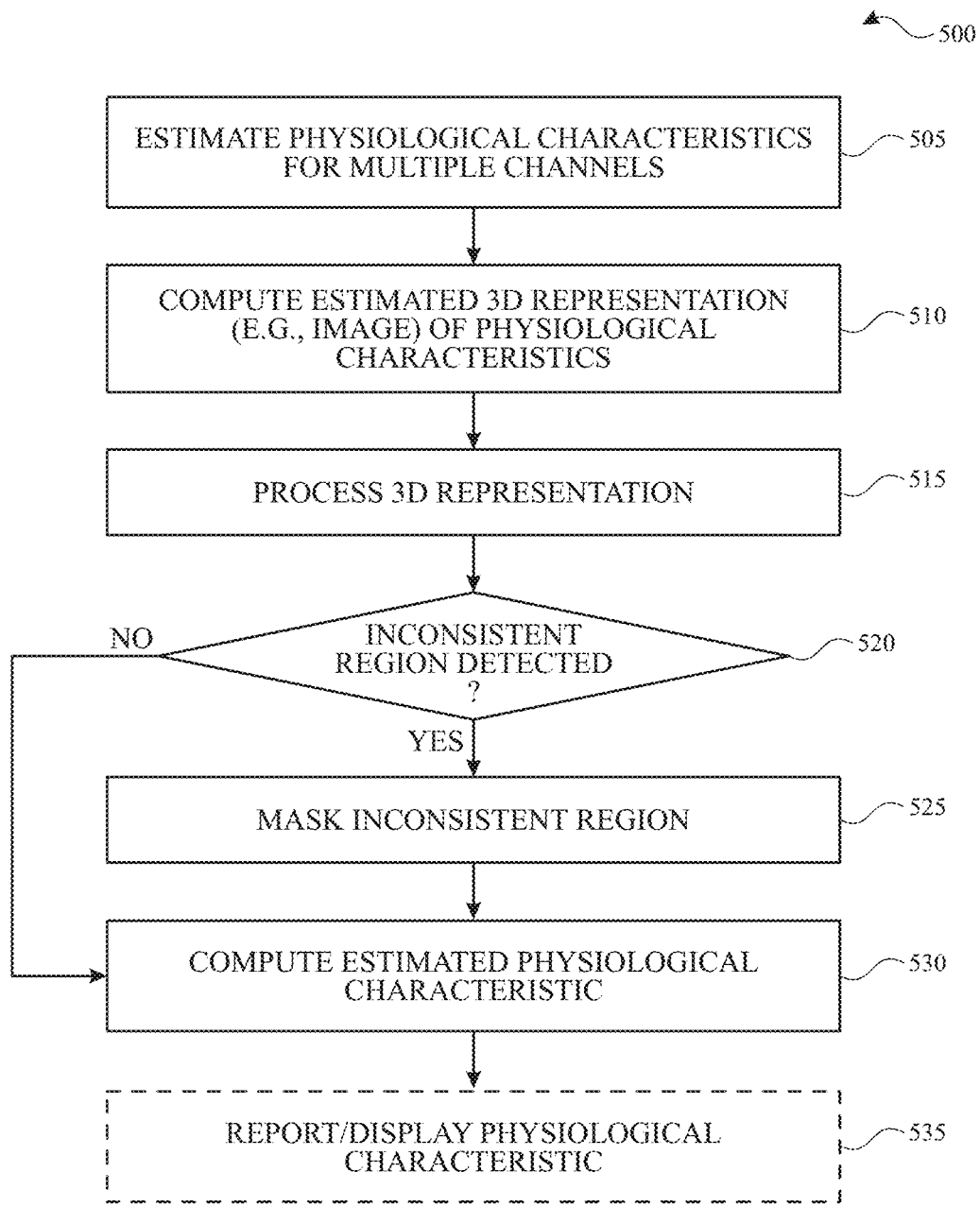
FIGS. 5A-5B illustrate an example process and an example block diagram for a measurement inconsistency mitigation algorithm according to examples of the disclosure.
Figure 5B:
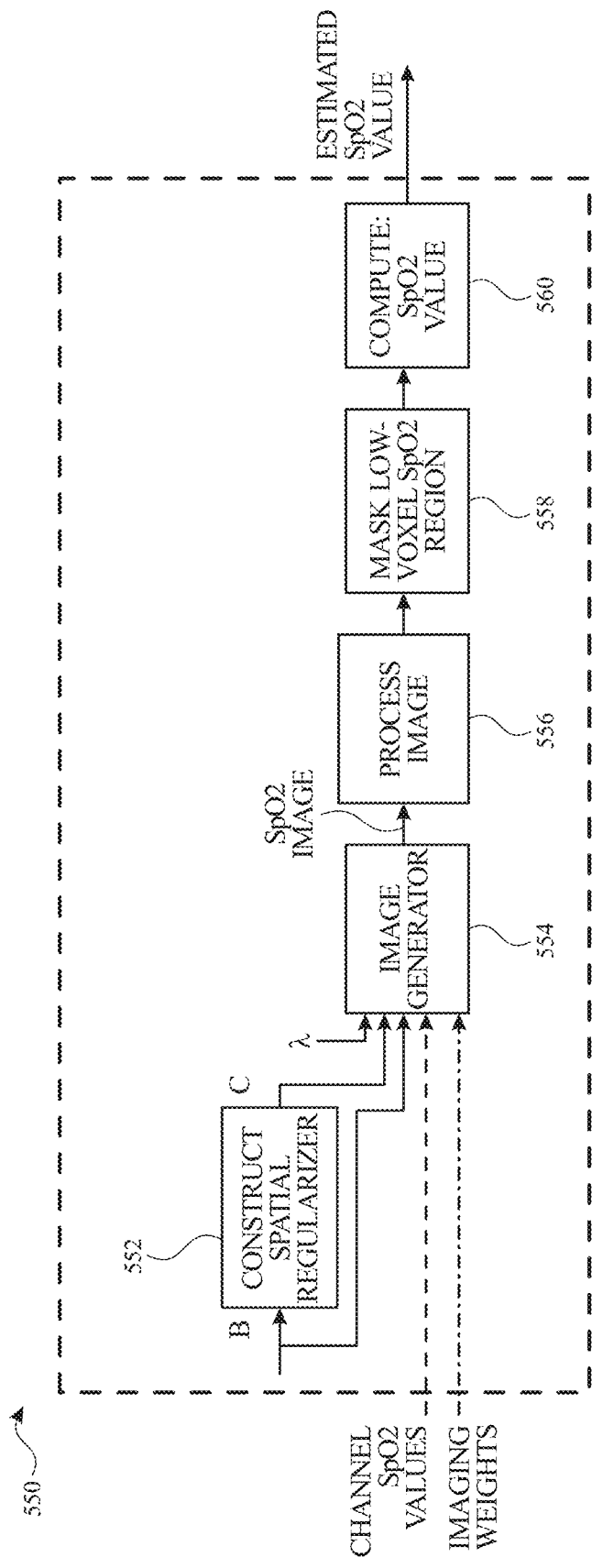

In some examples, a measurement inconsistency mitigation algorithm can be used to detect (e.g., from information about the cSpO2 values from multiple channels) and/or mitigate the spatially localized measurement inconsistency. FIGS. 5A-5B illustrate an example process 500 and an example block diagram 550 for a measurement inconsistency mitigation algorithm according to examples of the disclosure. At 505, physiological characteristics can be estimated for multiple channels. In some examples, the physiological characteristics are cSpO2 estimates for the multiple channels. For example, each channel of the optical sensor(s) 211 (e.g., channels 108, 110, 112, and 114 for the configuration of FIG. 1B, channels 158, 160, 162 and 164 for the configuration of FIG. 1D, or channels 178A-178I for the configuration of FIG. 1) can measure light at two different wavelengths (e.g., red and IR), and the cSpO2 is estimated for each channel using the perfusion index ratio between the measurements at the different wavelengths and using a correspondence between cSpO2 and the perfusion index ratio. At 510, a three-dimensional (3D) representation of the physiological characteristic can be computed, such as a 3D image modeling of the estimated local arterial oxygenation values for a region of tissue ("vSpO2" values, where v represents a voxel of the 3D image). At 515, the 3D representation (e.g., 3D image modeling vSpO2) can be processed to detect a spatially localized measurement inconsistency in a region of tissue. When a spatially localized measurement inconsistency is detected at 520 in a region ("an inconsistent region"), the inconsistent region can be masked from the 3D representation of at 525. At 530, an estimated physiological characteristic can be computed using the 3D representation without the masked inconsistent region. For example, the physiological characteristic can be computed by averaging the vSpO2 values at each voxel of the masked 3D representation. When a spatially localized measurement inconsistency is not detected at 520, an estimated physiological characteristic can be computed using the 3D representation without masking at 530, or alternatively the estimated physiological characteristic can be computed from the estimated physiological characteristics from the multiple channels directly without using the 3D representation from the measurement inconsistency mitigation algorithm. In some examples, the estimated physiological characteristic can be reported to the user at 535. For example, the estimated physiological characteristic can be displayed on the display, can be stored on the device or transmitted to another device, or can be reported with other feedback mechanisms (e.g., audio feedback, haptic feedback, etc.).

In some examples, the 3D representation of the physiological characteristic (e.g., 3D image) is generated using an inverse imaging techniques to estimate a vSpO2 value for each voxel in a 3D image based on relative contribution for different channels (optical paths) according to an expected distribution based on photon interaction with tissue for light traversing between the emitter and detector for the different channels, weighted for quality of the channel, and encouraged to constrain differences in vSpO2 between adjacent voxels. For example, a model for the inverse imaging problem can be defined by vector/matrix equation (1), in which the measured vSpO2 values are equated with a sensitivity map for the underlying tissue plus some noise:

$$y = Bs + \epsilon \qquad (1)$$

where y represents measurements of the physiological characteristics (e.g., cSpO2) for the multiple channels, B represents light interaction models of the multiple channels (e.g., density functions that describe the penetration of the photons from the emitter down into the tissue and back to the detector), s represents an estimate of underlying physiological characteristic (e.g., vSpO2) at each voxel of the 3D image, and e represents noise.

Figure 7A:
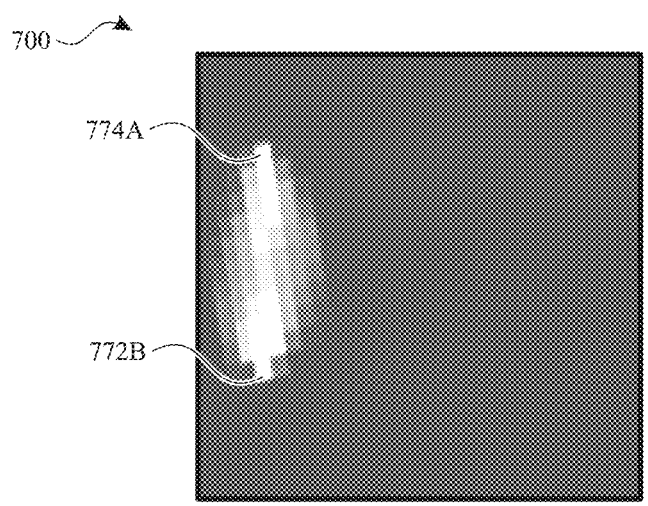
FIGS. 7A-7B illustrate example representations of a light interaction model representation for a channel according to examples of the disclosure.
Figure 7B:
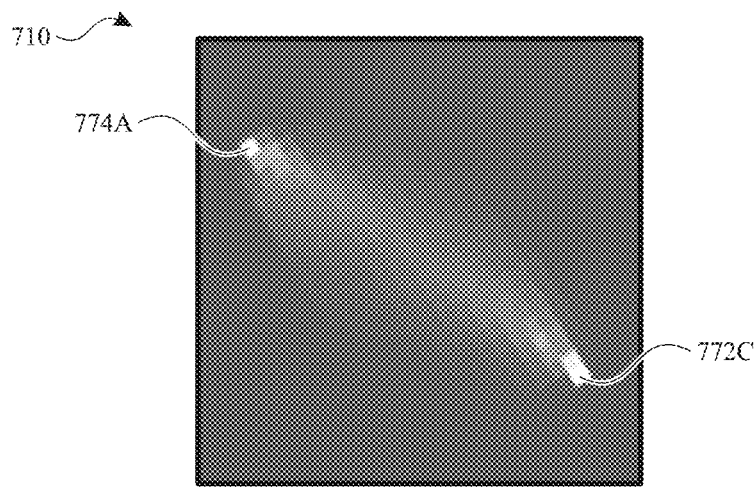

In some examples, the light interaction models can be photon banana models. In some examples, the photon banana models be simulated density functions driven by the geometry of the emitter and detector pairs for the given optical sensor hardware (defining photon interaction with the tissue that traces the region of tissue from the emitter to the detector). In some examples, the photon banana models generally model the light path(s) having a parabolic shape. Different emitter/detector pairs may probe different depths of the tissue. For example, more distant emitter/detector pairs may probe deeper regions of the tissue and therefore have a different density function. It is understood that the photon banana density functions are example sensitivity maps to estimate the amount of the measured vSpO2 along an light path to be attributed to the voxels, but other models may be used as light interaction models (e.g., based on empirical modeling). Example photo banana models are illustrated in FIGS. 7A-7B.

The solution to the inverse imaging problem can be defined as a cost function that minimizes a combination of a data fit expression and a spatial regularization expression. For example, equation (2) represents an example solution to the reverse imaging problem:

$$\hat{s} = \mathrm{argmin}\left(\frac{1}{2}\|y - Bs\|_W^2 + \lambda\|Cs\|^2\right) \qquad (2)$$

where ŝ represents the estimated 3D representation (e.g., 3D image), $$\frac{1}{2}\|y - Bs\|_W^2$$

represents the data fit expression, and $\lambda\|Cs\|^2$ represents the spatial regularization expression. Although the data fit and spatial regularization use L2 norms, it is understood that other solutions are possible that use different norms (e.g., L1 norms).

The data fit expression is a weighted norm of y-Bs, and provides an indication for how well an estimated image s fits the measurements y based on light interaction models B. The weighting applied for each channel is based on a quality metric for the measurement for each of the channels. As a result, the channels paths with relatively lower quality can be given less weight and those with relatively higher quality can be given more weight (e.g., enforcing data fitting more to the quality channels compares with lower quality channels). In some examples, the imaging weights can have values between zero and one, with higher values corresponding to physiologically valid PPG signals showing a consistent cardiac signal. In some examples, the PPG quality metric can be determined based on the signal-to-noise ratio (SNR) of the optical sensor hardware, the morphology of the PPG signals, the phase consistency between the PPG signals at different wavelengths (e.g., red, IR), correlation between the PPG signals at different wavelengths (e.g., red, IR), beat-to-beat consistency (correlation of heartbeats) in the PPG signal, and/or harmonic consistency.

The spatial regularization expression uses a difference operator, C, to penalize estimated 3D representation (e.g., 3D image), ŝ, with relatively high spatial variation or roughness. The spatial regularization is physiologically-motivated in part because large changes in vSpO2 in nearby tissue is not expected. Additionally, the spatial regularization expression improves the conditioning of the reverse imaging problem and increases the stability of the results. The conditioning may be particularly beneficial where the estimated 3D image ŝ has different, larger dimensions (and more unknowns) than y (which is limited to the number of measurement channels). In some examples, the spatial regularization expression may use other penalty operators (e.g., wavelet transforms) or a sum of multiple different penalty operators, In some examples, the reverse imaging problem can be further conditioned by constraining s between maximum and minimum constants representations. $\lambda$ represents a constant that balances the data fit expression and spatial regularization expression. Increasing 2 provides a smoother imager at the expense of a poorer data fit, whereas decreasing $\lambda$ provides a better data fit at the expense of a rougher image. $\lambda$ can be tuned empirically to optimize the accuracy of the measurement inconsistency mitigation algorithm. In some examples, $\lambda$ can vary across spatial dimensions x, y, and/or z, or 2 can vary as a function of the position in the image $s(x_i, y_i, z_i)$.

In some examples, the dimension of the 3D representation (3D image) can be based on the size and dimensions of the device and the arrangement of the light detectors and emitters. For example, the image size/dimensions can be based on the light interaction model (e.g., photon banana model) coverage for the channels of the device. In some examples, the 3D image can be defined using cubic/rectangular volume, and a mask can be used to focus on the regions of the tissue in which the light interaction models (e.g., photon banana models) indicate effective interaction with the tissue (excluding regions of the 3D representation of tissue that are not impacted by the optical sensor.

Process 500 can be performed at an electronic device such as device 100 or computing system 200 (e.g., by processor 210 and/or by signal processor 214). It should be understood that the particular order of the description of the operations in process is merely exemplary and is not intended to indicate that the described order is the only order in which the operations could be performed. One of ordinary skill in the art would recognize various ways to reorder the operations described herein (e.g., some operations of process 500 can be combined, reordered and/or omitted). For example, process 500 can receive estimated physiological characteristics and begin process 510 with generating the 3D representation based on the estimate physiological characteristics. Likewise, process 500 can omit reporting/displaying the physiological characteristics at 535.

FIG. 5B illustrates an example block diagram 550 for a measurement inconsistency mitigation algorithm corresponding to process 500. Block diagram 550 includes a construct spatial regularizer block 552 and image generator block 554 to generate the 3D representation (3D image) at 510 based on input parameters including the cSpO2 values for the multiple channels (e.g., estimated at 505) and their corresponding imaging weights, the light interaction models B (e.g., photon banana models), difference operators C, and parameter $\lambda$. The cSpO2 values and imaging weights for the multiple channels can be parameters computed/estimated for each measurement of cSpO2. The light interaction models B (e.g., photon banana models), difference operators C, and parameter 2 can be stored within the device for use in generating the 3D image. Image generator block 554 may perform an iterative algorithm to solve for an estimated 3D image balancing the data fitting expression and the spatial regularization expression as described with reference to equation (2).

Block diagram 550 includes an image processing block 556 to process the image to detect a spatially localized measurement inconsistency in a region (e.g., corresponding to 515 of process 500). Block diagram 550 includes a masking block 558 to mask an inconsistent region when a spatially localized measurement inconsistency is detected (e.g., corresponding to 525 of process 500), and a computation block 560 to compute the estimated physiological characteristic from the 3D representation without the masked inconsistent region (e.g., corresponding to 530 of process 500). The output of block diagram 550 can be the estimated SpO2 value. The blocks of block diagram 550 are, optionally, implemented by hardware, software, or a combination of hardware and software to carry out the principles of the various examples described herein. It is understood that the functional blocks of block diagram 550 can be, optionally, combined or separated into sub-blocks to implement the principles of the various examples described herein.

Figure 6A:
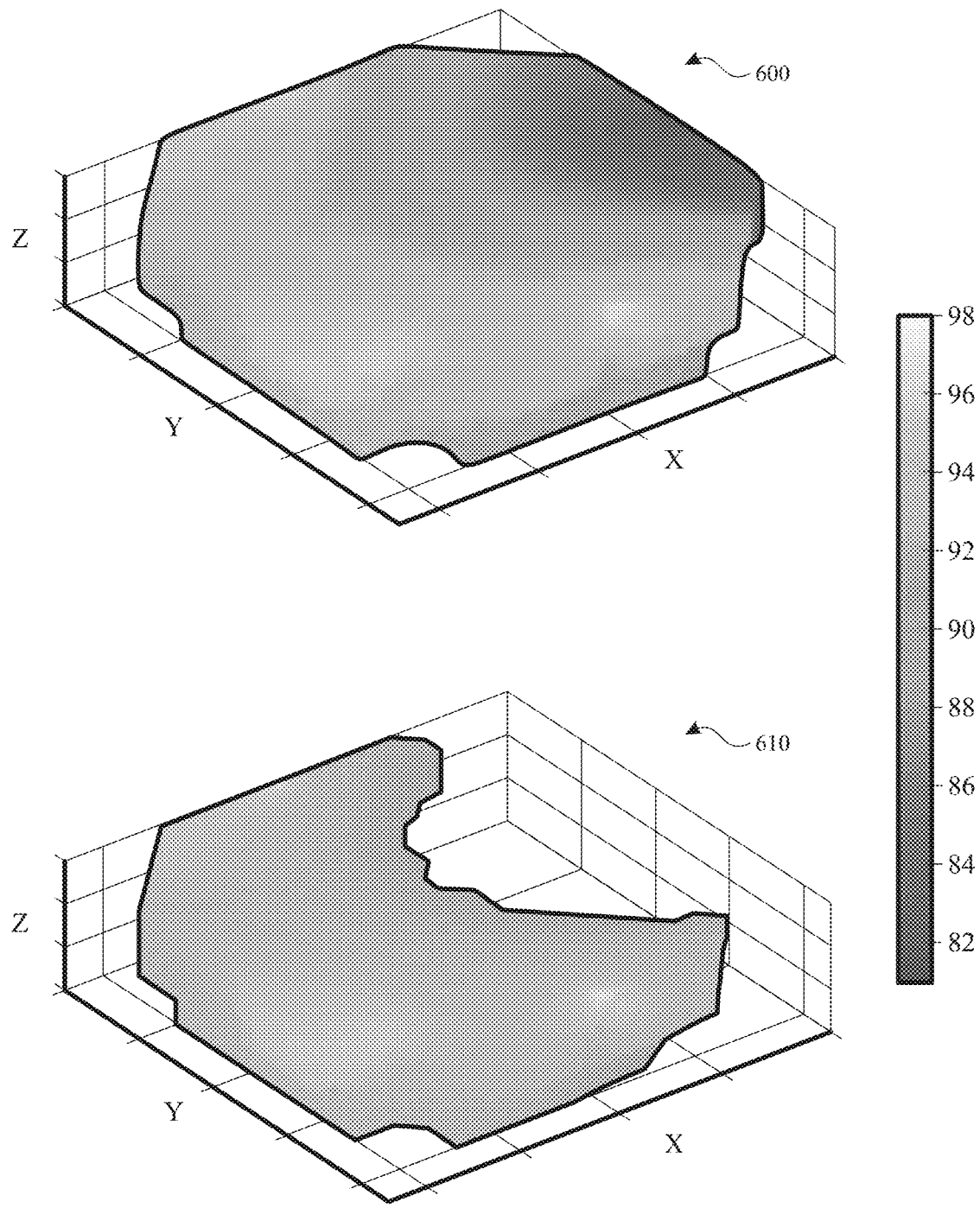
FIGS. 6A-6B illustrate an example three-dimensional representation of a physiological characteristic before and after masking according to examples of the disclosure.
Figure 6B:
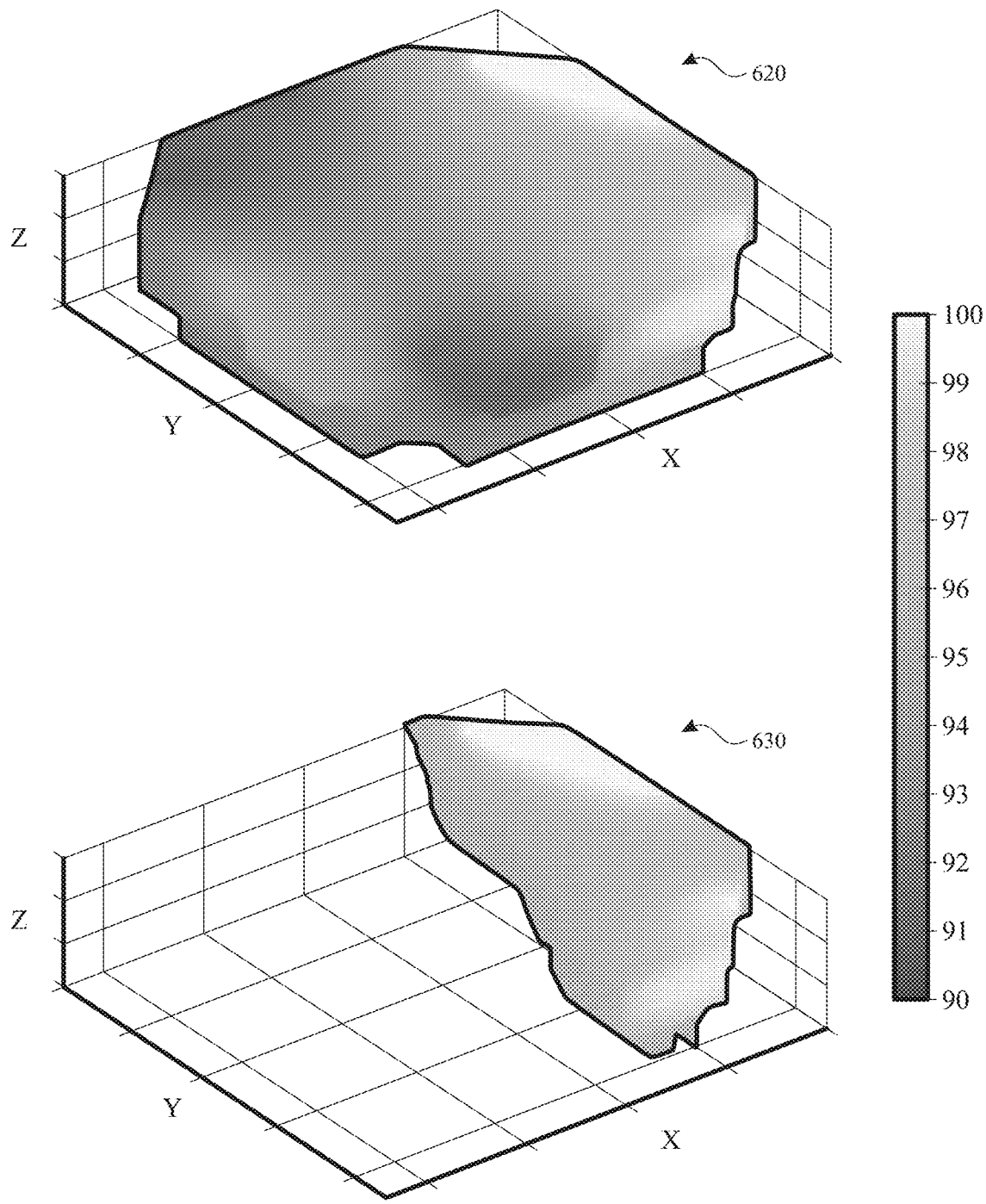

FIGS. 6A-6B illustrate an example 3D representations of vSpO2 before and after masking according to examples of the disclosure. FIG. 6A illustrates a 3D representation modeling vSpO2 for a region of tissue, 3D image 600, computed at 510 of process 500 based on cSpO2 values from multiple channels. FIG. 6A also illustrates a masked 3D representation modeling vSpO2 for a region of tissue, masked 3D image 610, corresponding to the masking at 525 of process 500. As shown in FIG. 6A, the masked region (included in 3D image 600 and excluded from 3D image 610) includes a spatially localized measurement inconsistency region including voxels with vSpO2 values that skew low compared with the rest of the 3D image. FIG. 6B illustrates a 3D representation modeling SpO2 for a region of tissue, 3D image 620, computed at 510 of process 500 based on vSpO2 values from multiple channels. FIG. 6B also illustrates a masked 3D representation modeling vSpO2 for a region of tissue, masked 3D image 630, corresponding to the masking at 525 of process 500. As shown in FIG. 6B, the masked region (included in 3D image 620 and excluded from 3D image 630) includes a spatially localized measurement inconsistency including voxels with vSpO2 values that skew low compared with the rest of the 3D image.

FIGS. 7A-7B illustrate example representations of a light interaction model representation (e.g., photon banana model) for a channel according to examples of the disclosure. Two-dimensional image 700 represents an example photon banana model. Image 700 is a compressed representation of a 3D photon banana model that shows the relative shape and density of for a light path between an emitter/detector pair corresponding to light emitter 172B and light detectors 174A of FIG. 1E (represented at locations 772B and 774A, respectively, in FIG. 7A). Image 710 is a compressed representation of a 3D photon banana model that shows the relative shape and density of for a light path between an emitter/detector pair corresponding to light emitter 172C and light detectors 174A of FIG. 1E (represented at locations 772C and 774A, respectively, in FIG. 7A). The two dimensional images 700 and 710 correspond to a top-down view of the tissue from the perspective of the underside of the device. Each pixel in the two dimensional image (representing the x-dimension and y-dimension) sums the values (relative intensity of light) for each layer of the 3D photon banana model in z-dimension. The longer path length represented in image 710 can be dimmer and can have a wider spread than the shorter path length represented in image 700 (where the light has less opportunity to interact with the tissue before being received by the detector). Images 700 and 710 are normalized with the brighter regions representing light with higher intensity compared with darker regions representing areas with lower intensity (or no intensity).

Figure 8:
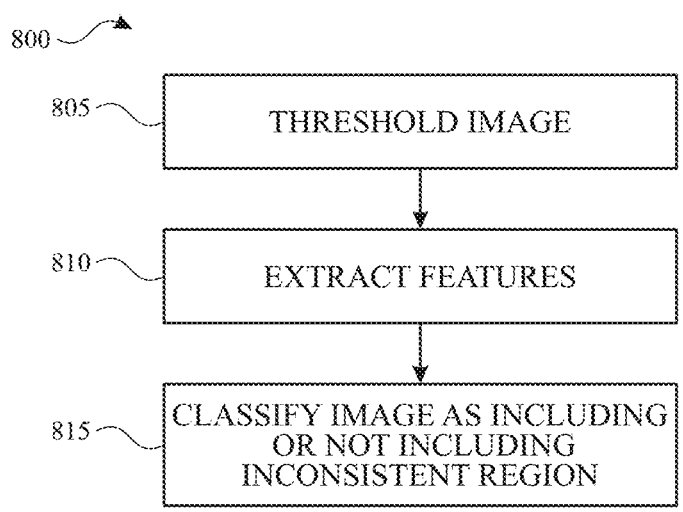
FIG. 8 illustrates an example process for processing an image as part of a measurement inconsistency mitigation algorithm according to examples of the disclosure.

FIG. 8 illustrates an example process 800 for processing an image for a measurement inconsistency mitigation algorithm according to examples of the disclosure. Process 800 can correspond to the image processing at 515 of the 3D image generated at 510 of process 500. At 805, the 3D image can be thresholded to generate a binary 3D image. For example, Otsu's method can be used to define a threshold to divide the voxels of the 3D image into two classes: "high" vSpO2 values and "low" vSpO2 values (e.g., minimizing the inter-class variance). At 810, features can be extracted from the binary 3D image. At 815, the extracted features can be used to classify the 3D image as including or not including a spatially localized measurement inconsistency. The details of process 800 are described in more detail below.

Figure 9:
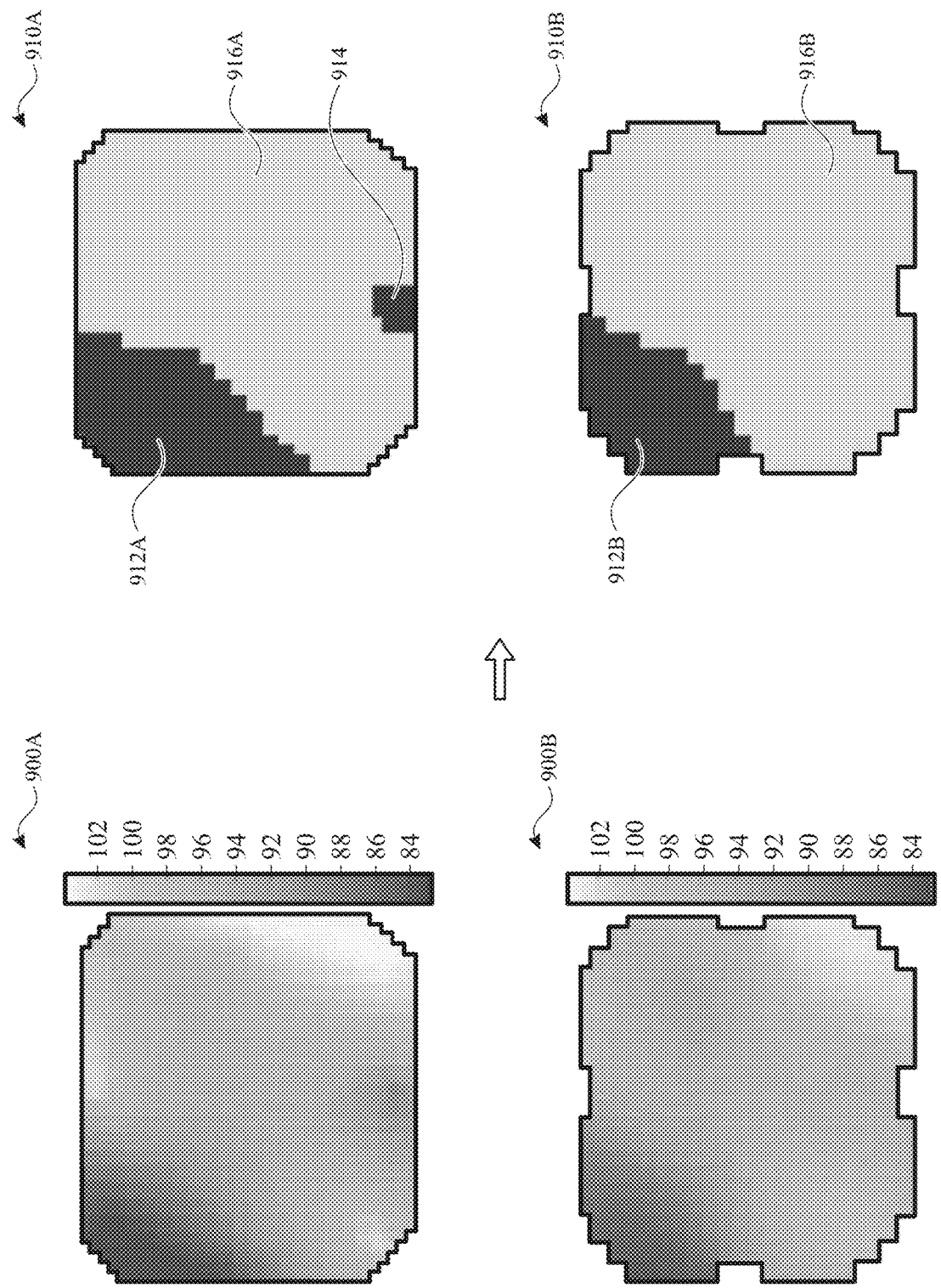
FIG. 9 illustrates an example of thresholding an image according to examples of the disclosure.

FIG. 9 illustrates an example of thresholding an image according to examples of the disclosure. FIG. 9 illustrates an example of processing a 3D image at 805 of process 800. Layers 900A and 900B are representative layers of an example 3D image of SpO2 values before thresholding. Layer 900A corresponds to a shallow depth within the tissue (e.g., a top layer) and layer 900B corresponds to a lower depth within the tissue (e.g., a bottom layer). Layers 910A and 910B are representative layers of the example 3D image of vSpO2 values after thresholding, with layer 910A corresponding to layer 900A and layer 910B corresponding to layer 900B. The binary 3D image divides the voxels into two classes, with the darker regions 912A, 912B, and 914 representative of "low" vSpO2 values and lighter regions 916A and 916B representative of high" vSpO2 values. Regions 912A-912B are indicative of a first cluster of low vSpO2 value voxels that appears to extend from layer 900A to layer 900B (e.g., from the top to the bottom) and region 914 is indicative of a second cluster of low vSpO2 value voxels shallow layer(s) near the top of the tissue, but that does not extend deeper within the tissue (e.g., does not extend to the bottom layers as it does not appear in layer 910B). In some examples, the 3D binary image can be filtered (e.g., using morphological image processing operations such as erosion and dilation) to reduce noise. In some examples, thresholding can be performed using image segmentation method that reduce boundary noise (e.g., using watershed segmentation).

The extracted features extracted at 810 of process 800 can include geometric properties of the cluster of either of the two classes in the binary 3D image. In some examples, the geometric properties can include measures of volume, surface area, compactness, contiguity, convexity and/or depth of the "low" vSpO2 cluster(s). For example, the compactness property can be estimated as the sphericity (e.g., ratio of volume to surface area) or using Bribiescas' measure for the "low" vSpO2 cluster(s). The contiguity property can be estimated using the number of connected "low" vSpO2 clusters and/or the fraction of volume belonging to the largest "low" vSpO2 cluster. In some examples, the contiguity property can also be measured used graph connectedness. The convexity property can be estimated as a solidity (e.g., a ratio of volume to the volume of the convex hull) of the "low" vSpO2 cluster(s). The depth property can be estimated as the centroid of the z-dimension of the "low" vSpO2 cluster (e.g., weighted according to the centroid in the x-y plane). A spatially localized measurement inconsistency often originates from deeper tissue regions and has high compactness, convexity and contiguity measures. Although the above geometric properties focus primarily on the "low" vSpO2 cluster(s), it should be understood that additionally or alternatively the geometric properties (e.g., compactness, etc.) can be estimated for "high" vSpO2 cluster(s).

Classifying the 3D image as including or not including a spatially localized measurement inconsistency can be implemented using a classifier. The classifier can receive the extracted features as inputs, and can output a binary classification of one of two possible states. One state can indicate that the 3D image includes a spatially localized measurement inconsistency, and another state can indicate that the 3D image does not include a spatially localized measurement inconsistency. In some examples, the classifier can output a probability that the 3D images includes (or does not include) a spatially localized measurement inconsistency. In some examples, the classifier can be implemented using machine learning techniques. For example, neural network (s), decision tree(s), logistical regression(s), etc. can be used to classify the 3D image as including or not including the spatially localized measurement inconsistency. The machine learning based classifier can be trained using training data that includes extracted features and labeled outputs to indicate whether the 3D image includes a spatially localized measurement inconsistency. The classification can be used to mask the 3D image to exclude a region with the spatially localized measurement inconsistency when such a spatially localized measurement inconsistency is detected (e.g., as described with respect to process 500 at 525).

As described herein, in some examples, a measurement inconsistency mitigation algorithm may be operative in the SpO2 estimation signal processing chain. For example, as illustrated in FIGS. 5A-5B, computing the estimated physiological characteristic (e.g., SpO2) can be based on the 3D image (whether masked or not). In some examples, when the measurement inconsistency mitigation algorithm detects no spatially localized measurement inconsistency, computing the estimated physiological characteristic (e.g., SpO2) can be based on the estimated physiological characteristics for multiple channels (e.g., without using the 3D image resulting from the measurement inconsistency mitigation algorithm). In some examples, the measurement inconsistency mitigation algorithm may be triggered and/or the output of the measurement inconsistency mitigation algorithm may be used to estimate SpO2 when the system cannot exclude the existence of a spatially localized measurement inconsistency. However, when the system can exclude the existence of a spatially localized measurement inconsistency (e.g., because it does not exist or does not meaningfully affect the estimated SpO2 measurement if it does exist), then the system can forgo triggering the measurement inconsistency mitigation algorithm and can compute the estimated physiological characteristic (e.g., SpO2) can be based on the estimated physiological characteristics for multiple channels (e.g., without using the 3D image). In some examples, the measurement inconsistency mitigation algorithm may be operative in the SpO2 estimation signal processing chain, but the measurement inconsistency mitigation algorithm may be aborted and/or the results of the measurement inconsistency mitigation algorithm may not be used to estimate SpO2 when the system can exclude the existence of a spatially localized measurement inconsistency. Triggering the measurement inconsistency mitigation algorithm and/or aborting the measurement inconsistency mitigation algorithm can reduce processing requirements and save power by forgoing the processing (e.g., generating and processing a 3D image) when unnecessary to achieve accurate pulse oximetry.

Figure 10:
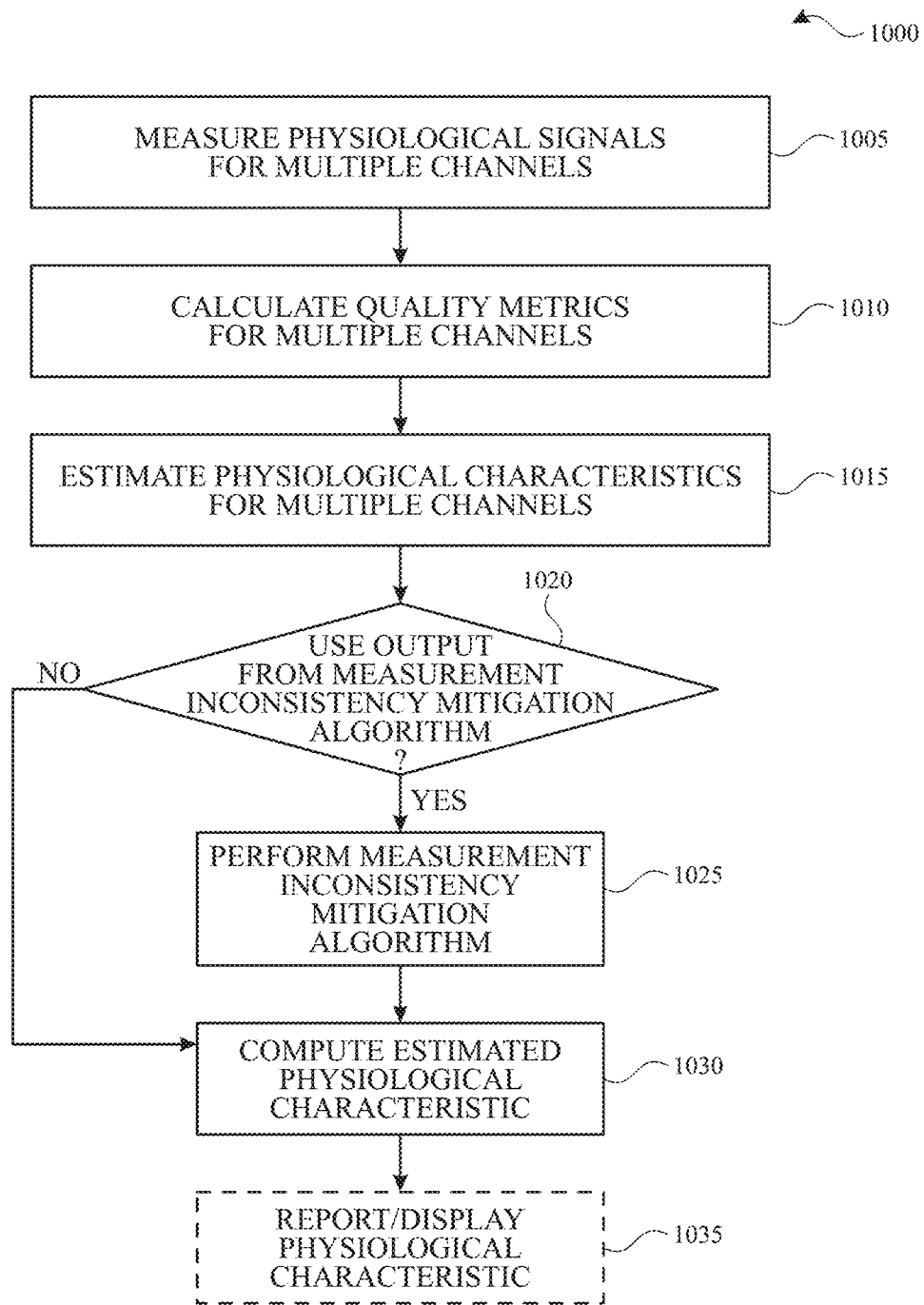
FIG. 10 illustrates an example process for estimating a physiological characteristic, optionally using a measurement inconsistency mitigation algorithm, according to examples of the disclosure.

FIG. 10 illustrates an example process 1000 for estimating a physiological characteristic, optionally using a measurement inconsistency mitigation algorithm, according to examples of the disclosure. At 1005, physiological signals can be measured for multiple channels. For example, each channel of the optical sensor(s) 211 (e.g., channels 108, 110, 112, and 114 for the configuration of FIG. 1B, channels 158, 160, 162 and 164 for the configuration of FIG. 1D, or channels 178A-178I for the configuration of FIG. 1) can measure light at two or more different wavelengths (e.g., red, IR, green, etc.). At 1010, one or more quality metrics can be calculated for the multiple channels. In some examples, larger imaging weights (e.g., between zero and one) can correspond to physiologically valid PPG signals showing a consistent cardiac signal. In some examples, the channel imaging weights can be determined based on one or more quality metrics including: the SNR of the optical sensor hardware, the morphology of the PPG signals, the phase consistency between the PPG signals at different wavelengths (e.g., red, IR, green), correlation between the PPG signals at different wavelengths (e.g., red, IR, green), beat-to-beat consistency (correlation of heartbeats) in the PPG signal, and/or harmonic consistency in the PPG signal. At 1015, physiological characteristics can be estimated for multiple channels. In some examples, a cSpO2 value is estimated for each channel (e.g., using the perfusion index ratio between the measurements at the different wavelengths and using a correspondence between cSpO2 and the perfusion index ratio).

At 1020, a determination can be made about whether to use an output from a measurement inconsistency mitigation algorithm. The determination can be performed using a signal processing algorithm of relatively less complexity than the image generation and processing of the measurement inconsistency mitigation algorithm. For example, the determination can be performed by a classifier configured to receive the measured physiological signals (at multiple wavelengths) for multiple channels, quality metrics for the multiple channels and/or physiological characteristics for the multiple channels. The classifier can output a binary classification of one of two possible states. One state can be indicative of the possibility of a spatially localized measurement inconsistency that meaningfully influences the estimate of the physiological characteristic (e.g., SpO2) and another state can be indicative of excluding the possibility of a spatially localized measurement inconsistency that meaningfully influence the estimate of the physiological characteristic. In some examples, the classifier can output a probability that the measurement data excludes the possibility a spatially localized measurement inconsistency. In some examples, the classifier can be implemented using machine learning techniques. For example, neural network(s), decision tree(s), logistical regression(s), etc. In some examples, features can be extracted from the measured physiological signals (at multiple wavelengths) for multiple channels, quality metrics for the multiple channels and/or physiological characteristics for the multiple channels. For example, the features may include features of the histogram (e.g., corresponding to histograms 400, 410), such as the maximum cSpO2 value, minimum cSpO2 value, mean cSpO2 value, mode cSpO2 value, median cSpO2 value, variance, and/or standard deviation, etc. The machine learning based classifier can be trained using training data that includes raw signals (e.g., measured physiological signals at multiple wavelengths for multiple channels, quality metrics for the multiple channels and/or physiological characteristics for the multiple channels) and/or extracted features and labeled outputs that indicate whether a spatially localized measurement inconsistency is present.

In accordance with a determination to use an output from a measurement inconsistency mitigation algorithm, the measurement inconsistency mitigation algorithm can be performed at 1025 (e.g., computing an estimated 3D representation of the physiological characteristics at 510, processing the 3D representation at 515, and masking an inconsistent region at 525 when an inconsistent region is detected at 520). At 1030, an estimated physiological characteristic can be computed by the 3D representation without the masked inconsistent region (e.g., corresponding to process 500 at 530). In accordance with a determination to not use an output from a measurement inconsistency mitigation algorithm, an estimated physiological characteristic can be computed from the estimated physiological characteristics of the multiple channels without using an output the measurement inconsistency mitigation algorithm and/or without performing the measurement inconsistency mitigation algorithm.

It should be understood that although FIG. 10 shows the determination about whether to use an output from a measurement inconsistency mitigation algorithm triggering the measurement inconsistency mitigation algorithm, in some examples, the measurement inconsistency mitigation algorithm can begin in parallel with the determination about whether to use an output from a measurement inconsistency mitigation algorithm, and the measurement inconsistency mitigation algorithm can be aborted in accordance with a determination not to use an output from a measurement inconsistency mitigation algorithm.

In some examples, the estimated physiological characteristic can be reported to the user at 1035. For example, the estimated physiological characteristic can be displayed on the display, stored on the device or transmitted to another device, or be reported with other feedback mechanisms (e.g., audio feedback, haptic feedback, etc.).

Process 1000 can be performed at an electronic device such as device 100 or computing system 200 (e.g., by processor 210 and/or by signal processor 214). It should be understood that the particular order of the description of the operations in process is merely exemplary and is not intended to indicate that the described order is the only order in which the operations could be performed. One of ordinary skill in the art would recognize various ways to reorder the operations described herein (e.g., some operations of process 1000 can be combined, reordered and/or omitted).

Figure 11:
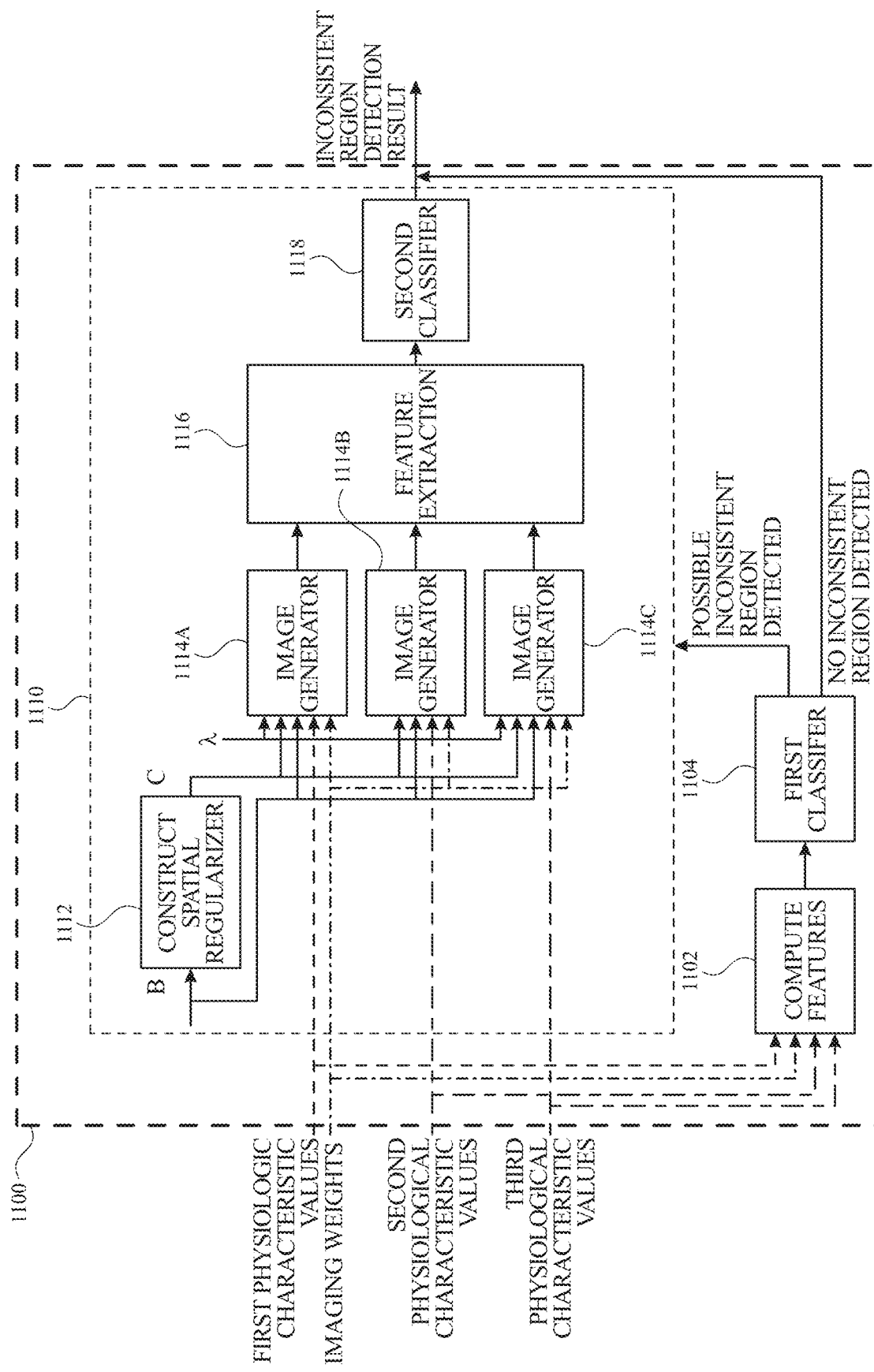
FIG. 11 illustrates an example block diagram for detection of a spatially localized measurement inconsistency according to examples of the disclosure.

In some examples, in order to improve robustness of estimating the physiological characteristic, different physiological characteristics can be estimated and used to detect and/or mitigate the impact of a spatially localized measurement inconsistency. FIG. 11 illustrates an example block diagram 1100 for detection of a spatially localized measurement inconsistency according to examples of the disclosure. Block diagram 1100 includes two classifiers related to spatially localized measurement inconsistency. The first classifier 1104 can be configured to perform a classification without image generation and processing and the second classifier 1118 can be configured to perform classification with image generation and processing. The second classification using image generation and processing can be computationally more intensive compared with the first classification without image generation and processing (and as a result may take longer and/or consume more power). As a result, the first classification can be used to trigger the second classification and/or to abort the second classification when such a second classification may be unnecessary (e.g., to avoid unnecessary processing, speed up the generation of a physiological characteristic estimate, and/or to save power).

In some example, as described above, the first and/or second classifications can be determined based on one physiological characteristic for multiple channels. For example, FIGS. 5A-5B and 10 describe classification based on cSpO2 values from multiple channels (and associated quality metrics/imaging weights for the multiple channels). In some examples, the first and/or second classifications can be determined based on multiple physiological characteristics for multiple channels (and associated quality metrics/ imaging weights for the multiple channels). For example, FIG. 11 illustrates a first classification and a second classification based on first physiological characteristic values, second physiological characteristic values, and third physiological characteristics values. In some examples, the first, second and third physiological characteristics can include cSpO2, a perfusion index (e.g., IR perfusion index), and a perfusion index ratio (e.g., green-to-IR perfusion index ratio).

In some examples, the first classifier 1104 can be based on features extracted from the first physiological characteristic values for multiple channels, the second physiological characteristic values for multiple channels, the third physiological characteristics values for multiple channels, and/or the imaging weights for multiple channels. For example, the features may include features such as the maximum cSpO2 value, minimum cSpO2 value, mean cSpO2 value, mode cSpO2 value, median cSpO2 value, variance of the cSpO2 values, standard deviation of the cSpO2 values, maximum IR perfusion index value, minimum IR perfusion index value, mean IR perfusion index value, mode IR perfusion index value, median IR perfusion index value, variance of the IR perfusion index values, standard deviation of the IR perfusion index values, maximum green/IR perfusion index ratio value, minimum green/IR perfusion index ratio value, mean green/IR perfusion index ratio value, mode green/IR perfusion index ratio value, median green/IR perfusion index ratio value, variance of green/IR perfusion index ratio values, and/or standard deviation of green/IR perfusion index ratio values, etc. First classifier 1104 can receive the features computed by the feature computation block 1102 and can output a classification as one of two possible states. One state can indicate detecting no spatially localized measurement inconsistency present (excluding the existence of a spatially localized measurement inconsistency because it does not exist or if it does exist does not meaningfully affect the estimated SpO2 measurement), and another state can indicate detecting a possible spatially localized measurement inconsistency present. In some examples, the first classifier 1104 can be implemented as a machine learning based classifier that can be trained using training data that includes extracted features (or the quality metrics for the multiple channels and physiological characteristics for the multiple channels) and labeled outputs that indicate whether a spatially localized measurement inconsistency is present.

In some examples, the second classification can be based on image generation and processing for the first physiological characteristic values for multiple channels, the second physiological characteristic values for multiple channels, the third physiological characteristics values for multiple channels, and/or the quality metrics/imaging weights for multiple channels. For example, a 3D image of vSpO2 values can be generated for cSpO2 values from multiple channels by image generator block 1114A and can be processed to extract features by feature extraction block 1116 (e.g., as described herein with respect to image processing block 556, image generator block 554, image processing at 515, thresholding at 805, and feature extraction at 810). The details of the image generation, image processing and feature extraction are not repeated here for brevity. In a similar manner, a 3D image of IR perfusion index can be generated (e.g., using the IR perfusion index values rather than the cSpO2 values for the multiple channels) by image generator block 1114B and can be processed to extract features by feature extraction block 1116, and a 3D image of green-to-IR perfusion index ratio can be generated (e.g., using the green-to-IR perfusion index ratio values rather than the cSpO2 values for the multiple channels) by image generator block 1114C and can be processed to extract features by feature extraction block 1116.

In some examples, the features extracted by feature extraction block 1116 for the IR perfusion index image and the green-to-IR perfusion index ratio image can be the same features extracted for the vSpO2 image (measures of volume, surface area, compactness, contiguity, convexity and/ or depth of the cluster(s)). In some examples, the extracted features can be different features for different physiological signal characteristic images. In some examples, the extract features include corroboration metrics between different 3D images. For example, the features can include a measure of agreement between the spatially localized region of tissue with "low" vSpO2 values in the binary image of vSpO2 and the spatially localized region of tissue with "high" IR perfusion in the binary image of IR perfusion index. In some examples, the features can include a measure of agreement between the 3D image of vSpO2 and the 3D image of IR perfusion index before thresholding (e.g., with agreement between lower vSpO2 values and higher IR PI values). In some examples, the features can include a measure of agreement between the spatially localized region of tissue with "low" vSpO2 values in the binary image of vSpO2 and the spatially localized region of tissue with "low" green-to-IR perfusion index ratio in the binary image of green-to-IR perfusion index ratio. In some examples, the features can include a measure of agreement between the 3D image of vSpO2 and the 3D image of green-to-IR perfusion index ratio before thresholding (e.g., with agreement between lower vSpO2 values and lower green-to-IR PI ratio values). In some examples, the measure of agreement can include performing a logical XOR operation between the binary 3D image of vSpO2 and the binary 3D image of IR perfusion index and then summing the voxels with an output of 1 from the logical XOR operation. In some examples, the measure of agreement can include performing a logical AND operation between the binary 3D image of vSpO2 and the binary 3D image of green-to-IR perfusion index ratio and then summing the voxels with an output of 1 from the logical AND operation. In some examples, the features can include a dynamic range of the IR perfusion index and/or of the green-to-IR perfusion index ratio.

In some examples, the second classification by second classifier 1118 can be based on features extracted by feature extraction block 1116. Second classifier 1118 can receive the features computed by the feature computation block 1116 and can output a classification as one of two possible states. One state can indicate detecting the presence of a spatially localized measurement inconsistency and another state can indicate detecting no measurement inconsistency present (because such a spatially localized measurement inconsistency does not exist or does not meaningfully affect the estimated SpO2 measurement if it does exist). The result of the classification can then be used, in some examples, to mask (or not mask) the 3D image of vSpO2 and to compute an estimate SpO2 measurement as described herein (e.g., at 530 of process 500). In some examples, the second classifier 1118 can be implemented as a machine learning based classifier that can be trained using training data that includes extracted features (or the raw signals or quality metrics for the multiple channels and physiological characteristics for the multiple channels) and labeled outputs that indicate whether a spatially localized measurement inconsistency is present. In some examples, the classification can be based on the geometric properties of the binary vSpO2 image and based on the agreement features with the IR perfusion index image and/or with green-to-IR perfusion index ratio image (e.g., the agreement between the "low" vSpO2 cluster and the "high" IR perfusion index cluster and/or the agreement between the "low" vSpO2 cluster and the "low" green-to-IR perfusion index ratio cluster).

The blocks of block diagram 1100 are, optionally, implemented by hardware, software, or a combination of hardware and software to carry out the principles of the various examples described herein. It is understood that the functional blocks of block diagram 1100 can be, optionally, combined or separated into sub-blocks to implement the principles of the various examples described herein. Additionally, it understood that block diagram 1100 can include more, fewer, or different blocks in some example. For example, the first and/or second classifiers can be performed with fewer than three different types of physiological characteristics and/or without feature extract blocks (e.g., using the raw physiological signals or computed physiological characteristics as inputs to the classifier(s)).

Although the measurement inconsistency mitigation algorithm to detect and/or mitigate a spatially localized measurement inconsistency is primarily described herein (e.g., with respect to FIG. 5A-5B and 1025) as including a 3D imaging techniques (e.g., computing a 3D representation of the physiological characteristic, such as a 3D image modeling vSpO2 values, and processing the 3D representation to detect a spatially localized measurement inconsistency in a region of tissue), it is understood that the measurement inconsistency mitigation algorithm to detect and/or mitigate a spatially localized measurement inconsistency can similarly be applied using two-dimensional (2D) imaging techniques. 2D imaging techniques may allow for identification and/or mitigation of spatially localized measurement inconsistency in a less computationally intensive manner (e.g., for improved speed and/or reduced power consumption).

For example, a 2D representation of the physiological characteristic can be computed, such as a 2D image modeling of the estimated local arterial oxygenation values for a region of tissue ("pSpO2" values, where p represents a pixel of the 2D image rather than "vSpO2" values, where v represents a voxel of the 3D image). The 2D representation (e.g., 2D image modeling pSpO2) can be processed to detect a spatially localized measurement inconsistency in a region of tissue, which can be mitigated by estimating the physiological characteristic using the 2D representation without the masked inconsistent region (e.g., by averaging the pSpO2 values at each pixel of the masked 2D representation. In some examples, the 2D representation of the physiological characteristic (e.g., 2D image) is generated using an inverse imaging techniques similar those described herein, but modified for two dimensions rather than three dimensions.

Although described above as 2D imaging techniques, it is understood that detecting and/or mitigating a spatially localized measurement inconsistency can be performed using a two-dimensional representation different than a 2D image. In some examples, the spatially localized measurement inconsistency can be spatially localized in that the inconsistency appears in a set of pre-defined spatially adjacent and/or overlapping channels). For example, rather than a 2D image with pixel SpO2 values (e.g., a cartesian representation), a 2D representation can be generated using weighted or unweighted groupings of cSpO2 values that derive from spatially adjacent emitter-detector pairs. The groupings can be based on adjacent channels (e.g., channels 178A-178B), common optical components (e.g., channels 178A, 178B, and 178H share light emitter 172A) and/or overlapping optically-probed regions (e.g., channels 178G, 178H, and 178I). In some examples, non-cartesian mapping can be used for generating a mask. The mask can identify spatially-adjacent emitter-detector pairs with respective cSpO2 values inconsistent to the others and/or can identify all cSpO2 values coming from a common emitter or detector that suggest similar or varying degrees of inconsistency. Optionally, the mask could be mapped to a cartesian-equivalent 2D image.

As discussed above, aspects in of the present technology include the gathering and use of physiological information. The technology may be implemented along with technologies that involve gathering personal data that relates to the user's health and/or uniquely identifies or can be used to contact or locate a specific person. Such personal data can include demographic data, date of birth, location-based data, telephone numbers, email addresses, home addresses, and data or records relating to a user's health or level of fitness (e.g., vital signs measurements, medication information, exercise information, etc.).

The present disclosure recognizes that a user's personal data, including physiological information, such as data generated and used by the present technology, can be used to the benefit of users. For example, monitoring physiological characteristics, such SpO2, may allow a user to track or otherwise gain insights about their health.

The present disclosure contemplates that the entities responsible for the collection, analysis, disclosure, transfer, storage, or other use of such personal data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should require receipt of the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. The policies and practices may be adapted depending on the geographic region and/or the particular type and nature of personal data being collected and used.

Despite the foregoing, the present disclosure also contemplates embodiments in which users selectively block the collection of, use of, or access to, personal data, including physiological information. For example, a user may be able to disable hardware and/or software elements that collect physiological information. Further, the present disclosure contemplates that hardware and/or software elements can be provided to prevent or block access to personal data that has already been collected. Specifically, users can select to remove, disable, or restrict access to certain health-related applications collecting users' personal health or fitness data.

Therefore, according to the above, some examples of the disclosure are directed to a method. The method can comprise: estimating a three-dimensional (3D) representation of physiological characteristics in tissue using physiological characteristics computed from measurements of a plurality of channels of an optical sensor, and processing the 3D representation. In accordance with a determination that the 3D representation includes a region that meets one or more criteria indicative of a spatially localized measurement inconsistency, computing an estimated physiological characteristic from the 3D representation excluding the region. Additionally or alternatively to one or more of the examples disclosed above, in some examples, the method can further comprise: in accordance with a determination that the 3D representation does not include the region that meets the one or more criteria, computing the estimated physiological characteristic from the 3D representation. Additionally or alternatively to one or more of the examples disclosed above, in some examples, estimating the 3D representation can comprise: estimating a physiological characteristic value for each voxel in the 3D representation based on relative contributions of the physiological characteristics from the plurality of channels of the optical sensor in accordance with expected distributions based on photon interactions within the tissue for the plurality of channels. Additionally or alternatively to one or more of the examples disclosed above, in some examples, the relative contributions of the physiological characteristics from the plurality of channels can be weighted in accordance with quality metrics of the plurality of channels. The relative contributions of the physiological characteristics from the plurality of channels can be estimated to constrain differences in the physiological characteristics between proximate voxels in the 3D representation. Additionally or alternatively to one or more of the examples disclosed above, in some examples, processing the 3D representation can comprises: thresholding the 3D representation to generate a binary 3D representation; extracting features of the binary 3D representation; and classifying whether the 3D representation includes the region that meets the one or more criteria using the extracted features. Additionally or alternatively to one or more of the examples disclosed above, in some examples, the features of the binary representation include geometric features. Additionally or alternatively to one or more of the examples disclosed above, in some examples, the geometric features can include a compactness feature, a contiguity feature, a convexity feature or a depth feature. Some examples of the disclosure are directed to a non-transitory computer readable storage medium. The non-transitory computer readable storage medium can store instructions, which when executed by an electronic device comprising processing circuitry, can cause the processing circuitry to perform any of the above methods.

Some examples of the disclosure are directed to an electronic device (e.g., a wearable device). The electronic device can comprise an optical sensor including a plurality of channels and a processor coupled to the optical sensor. The processor (processing circuitry) can be programmed to: estimate a three-dimensional (3D) representation of physiological characteristics in tissue using physiological characteristics computed from measurements of a plurality of channels of an optical sensor and process the 3D representation. The processor can be further programmed to: in accordance with a determination that the 3D representation includes a region that meets one or more criteria indicative of a spatially localized measurement inconsistency, compute an estimated physiological characteristic from the 3D representation excluding the region. Additionally or alternatively to one or more of the examples disclosed above, in some examples, the processor can be further programmed to: in accordance with a determination that the 3D representation does not include the region that meets the one or more criteria, compute the estimated physiological characteristic from the 3D representation. Additionally or alternatively to one or more of the examples disclosed above, in some examples, estimating the 3D representation can comprise: estimating a physiological characteristic value for each voxel in the 3D representation based on relative contributions of the physiological characteristics from the plurality of channels of the optical sensor in accordance with expected distributions based on photon interactions within the tissue for the plurality of channels. Additionally or alternatively to one or more of the examples disclosed above, in some examples, the relative contributions of the physiological characteristics from the plurality of channels can be weighted in accordance with quality metrics of the plurality of channels. The relative contributions of the physiological characteristics from the plurality of channels can be estimated to constrain differences in the physiological characteristics between proximate voxels in the 3D representation. Additionally or alternatively to one or more of the examples disclosed above, in some examples, processing the 3D representation can comprise: thresholding the 3D representation to generate a binary 3D representation; extracting features of the binary 3D representation; and classifying whether the 3D representation includes the region that meets the one or more criteria using the extracted features. Additionally or alternatively to one or more of the examples disclosed above, in some examples, the features of the binary representation can include geometric features. Additionally or alternatively to one or more of the examples disclosed above, in some examples, the geometric features can include a compactness feature, a contiguity feature, a convexity feature or a depth feature.

Some examples of the disclosure are directed to an electronic device (e.g., a wearable device). The electronic device can comprise: an optical sensor including a plurality of channels; and a processor coupled to the optical sensor. The processor (e.g., processing circuitry) can be programmed to: in accordance with a determination to use an output of a measurement inconsistency mitigation algorithm, compute an estimated physiological characteristic using the output of measurement inconsistency mitigation algorithm; and in accordance with a determination to not use the output of the measurement inconsistency mitigation algorithm, compute the estimated physiological characteristic without using the output of the measurement inconsistency mitigation algorithm. Additionally or alternatively to one or more of the examples disclosed above, in some examples, the processor can be further programmed to: compute a plurality of first physiological characteristics for the plurality of channels; estimate a first three-dimensional (3D) representation of a first physiological characteristics in tissue based on the plurality of first physiological characteristics; process the first 3D representation; and in accordance with a determination that the 3D representation includes a region that meets one or more criteria indicative of a spatially localized measurement inconsistency, compute the estimated physiological characteristic from the 3D representation excluding the region. Additionally or alternatively to one or more of the examples disclosed above, in some examples, the processor can be further programmed to:

compute a plurality of first physiological characteristics for the plurality of channels, a plurality of second physiological characteristics for the plurality of channels, and a plurality of third physiological characteristics for the plurality of channels; estimate a first 3D representation of a first physiological characteristic in tissue based on the plurality of first physiological characteristics, a second 3D representation of a second physiological characteristic in tissue based on the plurality of second physiological characteristics, a third 3D representation of a third physiological characteristic in tissue based on the plurality of third physiological characteristics; process the first 3D representation, the second representation and the third representation; and in accordance with a determination that the 3D representation of the first physiological characteristic includes a region that meets one or more criteria indicative of a spatially localized measurement inconsistency, the one or more criteria including an indication of spatial agreement between the 3D representation of the first physiological characteristic and the 3D representation of the second physiological characteristic or the 3D representation of the third physiological characteristic, compute the estimated physiological characteristic from the 3D representation of the first physiological characteristic excluding the region. Additionally or alternatively to one or more of the examples disclosed above, in some examples, the determination of whether to use or not use the output of the measurement inconsistency mitigation algorithm can comprise: computing a plurality of first physiological characteristics for the plurality of channels, a plurality of second physiological characteristics for the plurality of channels, and a plurality of third physiological characteristics for the plurality of channels; and extracting features of the plurality of first physiological characteristics for the plurality of channels, the plurality of second physiological characteristics for the plurality of channels, and the plurality of third physiological characteristics for the plurality of channels. Additionally or alternatively to one or more of the examples disclosed above, in some examples, the processor can be further programmed to: in accordance with the determination to use the output of the measurement inconsistency mitigation algorithm, trigger the measurement inconsistency mitigation algorithm. Additionally or alternatively to one or more of the examples disclosed above, in some examples, the processor can be further programmed to: in accordance with the determination to not use the output of the measurement inconsistency mitigation algorithm, abort the measurement inconsistency mitigation algorithm.

Some examples of the disclosure are directed to a method. The method can comprise: in accordance with a determination to use an output of a measurement inconsistency mitigation algorithm, computing an estimated physiological characteristic using the output of measurement inconsistency mitigation algorithm; and in accordance with a determination to not use the output of the measurement inconsistency mitigation algorithm, computing the estimated physiological characteristic without using the output of the measurement inconsistency mitigation algorithm. Additionally or alternatively to one or more of the examples disclosed above, in some examples, the method can further comprise: computing a plurality of first physiological characteristics for the plurality of channels; estimating a first three-dimensional (3D) representation of a first physiological characteristics in tissue based on the plurality of first physiological characteristics; processing the first 3D representation; and in accordance with a determination that the 3D representation includes a region that meets one or more criteria indicative of a spatially localized measurement inconsistency, computing the estimated physiological characteristic from the 3D representation excluding the region. Additionally or alternatively to one or more of the examples disclosed above, in some examples, the method can further comprise: computing a plurality of first physiological characteristics for the plurality of channels, a plurality of second physiological characteristics for the plurality of channels, and a plurality of third physiological characteristics for the plurality of channels; estimating a first 3D representation of a first physiological characteristic in tissue based on the plurality of first physiological characteristics, a second 3D representation of a second physiological characteristic in tissue based on the plurality of second physiological characteristics, a third 3D representation of a third physiological characteristic in tissue based on the plurality of third physiological characteristics; processing the first 3D representation, the second representation and the third representation; and in accordance with a determination that the 3D representation of the first physiological characteristic includes a region that meets one or more criteria indicative of a spatially localized measurement inconsistency, the one or more criteria including an indication of spatial agreement between the 3D representation of the first physiological characteristic and the 3D representation of the second physiological characteristic or the 3D representation of the third physiological characteristic, computing the estimated physiological characteristic from the 3D representation of the first physiological characteristic excluding the region. Additionally or alternatively to one or more of the examples disclosed above, in some examples, the determination of whether to use or not use the output of the measurement inconsistency mitigation algorithm can comprise: computing a plurality of first physiological characteristics for the plurality of channels, a plurality of second physiological characteristics for the plurality of channels, and a plurality of third physiological characteristics for the plurality of channels; and extracting features of the plurality of first physiological characteristics for the plurality of channels, the plurality of second physiological characteristics for the plurality of channels, and the plurality of third physiological characteristics for the plurality of channels. Additionally or alternatively to one or more of the examples disclosed above, in some examples, the method can further comprise: in accordance with the determination to use the output of the measurement inconsistency mitigation algorithm, triggering the measurement inconsistency mitigation algorithm. Additionally or alternatively to one or more of the examples disclosed above, in some examples, the method can further comprise: in accordance with the determination to not use the output of the measurement inconsistency mitigation algorithm, aborting the measurement inconsistency mitigation algorithm. Some examples of the disclosure are directed to a non-transitory computer readable storage medium. The non-transitory computer readable storage medium can store instructions, which when executed by an electronic device comprising processing circuitry, can cause the processing circuitry to perform any of the above methods.

Therefore, according to the above, some examples of the disclosure are directed to a method. The method can comprise: estimating a multi-dimensional representation (e.g., a two-dimensional representation or a three-dimensional representation) of physiological characteristics in tissue using physiological characteristics computed from measurements of a plurality of channels of an optical sensor, and processing the multi-dimensional representation. In accordance with a determination that the multi-dimensional representation includes a region that meets one or more criteria indicative of a spatially localized measurement inconsistency, computing an estimated physiological characteristic from the multi-dimensional representation excluding the region. Additionally or alternatively to one or more of the examples disclosed above, in some examples, the method can further comprise: in accordance with a determination that the multi-dimensional representation does not include the region that meets the one or more criteria, computing the estimated physiological characteristic from the multi-dimensional representation. Additionally or alternatively to one or more of the examples disclosed above, in some examples, estimating the multi-dimensional representation can comprise: estimating a physiological characteristic value for each voxel in a 3D representation based on relative contributions of the physiological characteristics from the plurality of channels of the optical sensor in accordance with expected distributions based on photon interactions within the tissue for the plurality of channels. Additionally or alternatively to one or more of the examples disclosed above, in some examples, the relative contributions of the physiological characteristics from the plurality of channels can be weighted in accordance with quality metrics of the plurality of channels. The relative contributions of the physiological characteristics from the plurality of channels can be estimated to constrain differences in the physiological characteristics between proximate voxels in the 3D representation. Additionally or alternatively to one or more of the examples disclosed above, in some examples, processing the 3D representation can comprises: thresholding a 3D representation to generate a binary 3D representation; extracting features of the binary 3D representation; and classifying whether the 3D representation includes the region that meets the one or more criteria using the extracted features. Additionally or alternatively to one or more of the examples disclosed above, in some examples, the features of the binary representation include geometric features. Additionally or alternatively to one or more of the examples disclosed above, in some examples, the geometric features can include a compactness feature, a contiguity feature, a convexity feature or a depth feature. Some examples of the disclosure are directed to a non-transitory computer readable storage medium. The non-transitory computer readable storage medium can store instructions, which when executed by an electronic device comprising processing circuitry, can cause the processing circuitry to perform any of the above methods.

Some examples of the disclosure are directed to an electronic device (e.g., a wearable device). The electronic device can comprise an optical sensor including a plurality of channels and a processor coupled to the optical sensor. The processor (processing circuitry) can be programmed to: estimate a multi-dimensional representation (e.g., a two-dimensional representation or a three-dimensional representation) of physiological characteristics in tissue using physiological characteristics computed from measurements of a plurality of channels of an optical sensor and process the multi-dimensional representation. The processor can be further programmed to: in accordance with a determination that the multi-dimensional representation includes a region that meets one or more criteria indicative of a spatially localized measurement inconsistency, compute an estimated physiological characteristic from the multi-dimensional representation excluding the region. Additionally or alternatively to one or more of the examples disclosed above, in some examples, the processor can be further programmed to: in accordance with a determination that the multi-dimensional representation does not include the region that meets the one or more criteria, compute the estimated physiological char-acteristic from the multi-dimensional representation. Additionally or alternatively to one or more of the examples disclosed above, in some examples, estimating the multi-dimensional representation can comprise: estimating a physiological characteristic value for each voxel in a 3D representation based on relative contributions of the physiological characteristics from the plurality of channels of the optical sensor in accordance with expected distributions based on photon interactions within the tissue for the plurality of channels. Additionally or alternatively to one or more of the examples disclosed above, in some examples, the relative contributions of the physiological characteristics from the plurality of channels can be weighted in accordance with quality metrics of the plurality of channels. The relative contributions of the physiological characteristics from the plurality of channels can be estimated to constrain differences in the physiological characteristics between proximate voxels in the 3D representation. Additionally or alternatively to one or more of the examples disclosed above, in some examples, processing a 3D representation can comprise: thresholding the 3D representation to generate a binary 3D representation; extracting features of the binary 3D representation; and classifying whether the 3D representation includes the region that meets the one or more criteria using the extracted features. Additionally or alternatively to one or more of the examples disclosed above, in some examples, the features of the binary representation can include geometric features. Additionally or alternatively to one or more of the examples disclosed above, in some examples, the geometric features can include a compactness feature, a contiguity feature, a convexity feature or a depth feature.

Some examples of the disclosure are directed to a method. The method can comprise: in accordance with a determination to use an output of a measurement inconsistency mitigation algorithm, computing an estimated physiological characteristic using the output of measurement inconsistency mitigation algorithm; and in accordance with a determination to not use the output of the measurement inconsistency mitigation algorithm, computing the estimated physiological characteristic without using the output of the measurement inconsistency mitigation algorithm. Additionally or alternatively to one or more of the examples disclosed above, in some examples, the method can further comprise: computing a plurality of first physiological characteristics for the plurality of channels; estimating a first multi-dimensional representation (e.g., a two-dimensional representation or a three-dimensional representation) of a first physiological characteristics in tissue based on the plurality of first physiological characteristics; processing the first multi-dimensional representation; and in accordance with a determination that the multi-dimensional representation includes a region that meets one or more criteria indicative of a spatially localized measurement inconsistency, computing the estimated physiological characteristic from the multi-dimensional representation excluding the region. Additionally or alternatively to one or more of the examples disclosed above, in some examples, the method can further comprise: computing a plurality of first physiological characteristics for the plurality of channels, a plurality of second physiological characteristics for the plurality of channels, and a plurality of third physiological characteristics for the plurality of channels; estimating a first multi-dimensional representation of a first physiological characteristic in tissue based on the plurality of first physiological characteristics, a second multi-dimensional representation of a second physiological characteristic in tissue based on the plurality of second physiological characteristics, a third multi-dimensional representation of a third physiological characteristic in tissue based on the plurality of third physiological characteristics; processing the first multi-dimensional representation, the second multi-dimensional representation and the third multi-dimensional representation; and in accordance with a determination that the multi-dimensional representation of the first physiological characteristic includes a region that meets one or more criteria indicative of a spatially localized measurement inconsistency, the one or more criteria including an indication of spatial agreement between the multi-dimensional representation of the first physiological characteristic and the multi-dimensional representation of the second physiological characteristic or the multi-dimensional representation of the third physiological characteristic, computing the estimated physiological characteristic from the multi-dimensional representation of the first physiological characteristic excluding the region. Additionally or alternatively to one or more of the examples disclosed above, in some examples, the determination of whether to use or not use the output of the measurement inconsistency mitigation algorithm can comprise: computing a plurality of first physiological characteristics for the plurality of channels, a plurality of second physiological characteristics for the plurality of channels, and a plurality of third physiological characteristics for the plurality of channels; and extracting features of the plurality of first physiological characteristics for the plurality of channels, the plurality of second physiological characteristics for the plurality of channels, and the plurality of third physiological characteristics for the plurality of channels. Additionally or alternatively to one or more of the examples disclosed above, in some examples, the method can further comprise: in accordance with the determination to use the output of the measurement inconsistency mitigation algorithm, triggering the measurement inconsistency mitigation algorithm. Additionally or alternatively to one or more of the examples disclosed above, in some examples, the method can further comprise: in accordance with the determination to not use the output of the measurement inconsistency mitigation algorithm, aborting the measurement inconsistency mitigation algorithm. Some examples of the disclosure are directed to a non-transitory computer readable storage medium. The non-transitory computer readable storage medium can store instructions, which when executed by an electronic device comprising processing circuitry, can cause the processing circuitry to perform any of the above methods.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

The invention claimed is:

1. A method comprising:
at a device in communication with an optical sensor including a plurality of light detectors and a plurality of light emitters:
emitting light from the plurality of light emitters;
detecting light at the plurality of light detectors;
estimating a multi-dimensional representation of physiological characteristics in tissue using physiological characteristics computed from measurements of a plurality of channels of the optical sensor, each of the plurality of channels corresponding to at least one of the plurality of light emitters and at least one of the plurality of light detectors;

processing the multi-dimensional representation;
in accordance with a determination that the multi-dimensional representation includes a region that meets one or more criteria indicative of a spatially localized measurement inconsistency:
computing an estimated physiological characteristic from the multi-dimensional representation excluding the region.

2. The method of claim 1, further comprising:
in accordance with a determination that the multi-dimensional representation does not include the region that meets the one or more criteria:
computing the estimated physiological characteristic from the multi-dimensional representation.

3. The method of claim 1, wherein estimating the multi-dimensional representation comprises:
estimating a physiological characteristic value for each voxel in a three-dimensional (3D) representation based on relative contributions of the physiological characteristics from the plurality of channels of the optical sensor in accordance with expected distributions based on photon interactions within the tissue for the plurality of channels.

4. The method of claim 3, wherein the relative contributions of the physiological characteristics from the plurality of channels are weighted in accordance with quality metrics of the plurality of channels, and wherein the relative contributions of the physiological characteristics from the plurality of channels are estimated to constrain differences in the physiological characteristics between proximate voxels in the 3D representation.

5. The method of claim 1, wherein processing the multi-dimensional representation comprises:
thresholding a 3D representation to generate a binary 3D representation;
extracting features of the binary 3D representation; and
classifying whether the 3D representation includes the region that meets the one or more criteria using the extracted features.

6. The method of claim 5, wherein the features of the 3D binary representation include geometric features.

7. The method of claim 6, wherein the geometric features include a compactness feature, a contiguity feature, a convexity feature or a depth feature.

8. An electronic device comprising:
an optical sensor including a plurality of channels, a plurality of light detectors and a plurality of light emitters; and
a processor coupled to the optical sensor programmed to:
emit light from the plurality of light emitters;
detect light at the plurality of light detectors;
estimate a multi-dimensional representation of physiological characteristics in tissue using physiological characteristics computed from measurements of the plurality of channels of the optical sensor, each of the plurality of channels corresponding to at least one of the plurality of light emitters and at least one of the plurality of light detectors;
process the multi-dimensional representation;
in accordance with a determination that the multi-dimensional representation includes a region that meets one or more criteria indicative of a spatially localized measurement inconsistency:
compute an estimated physiological characteristic from the multi-dimensional representation excluding the region.

9. The electronic device of claim 8, the processor further programmed to:
in accordance with a determination that the multi-dimensional representation does not include the region that meets the one or more criteria:
compute the estimated physiological characteristic from the multi-dimensional representation.

10. The electronic device of claim 8, wherein estimating the multi-dimensional representation comprises:
estimating a physiological characteristic value for each voxel in a three-dimensional (3D) representation based on relative contributions of the physiological characteristics from the plurality of channels of the optical sensor in accordance with expected distributions based on photon interactions within the tissue for the plurality of channels.

11. The electronic device of claim 10, wherein the relative contributions of the physiological characteristics from the plurality of channels are weighted in accordance with quality metrics of the plurality of channels, and wherein the relative contributions of the physiological characteristics from the plurality of channels are estimated to constrain differences in the physiological characteristics between proximate voxels in the 3D representation.

12. The electronic device of claim 8, wherein processing the multi-dimensional representation comprises:
thresholding a 3D representation to generate a binary 3D representation;
extracting features of the binary 3D representation; and
classifying whether the 3D representation includes the region that meets the one or more criteria using the extracted features.

13. The electronic device of claim 12, wherein the features of the binary 3D representation include geometric features.

14. The electronic device of claim 13, wherein the geometric features include a compactness feature, a contiguity feature, a convexity feature or a depth feature.

15. A non-transitory computer readable storage medium storing instructions, which when executed by an electronic device including an optical sensor including a plurality of channels, a plurality of light detectors, a plurality of light emitters and processing circuitry, cause the processing circuitry to:
emit light from the plurality of light emitters;
detect light at the plurality of light detectors;
estimate a multi-dimensional representation of physiological characteristics in tissue using physiological characteristics computed from measurements of the plurality of channels of the optical sensor, each of the plurality of channels corresponding to at least one of the plurality of light emitters and at least one of the plurality of light detectors;
process the multi-dimensional representation;
in accordance with a determination that the multi-dimensional representation includes a region that meets one or more criteria indicative of a spatially localized measurement inconsistency:
compute an estimated physiological characteristic from the multi-dimensional representation excluding the region.

16. The non-transitory computer readable storage medium of claim 15, the processing circuitry further programmed to:
in accordance with a determination that the multi-dimensional representation does not include the region that meets the one or more criteria:
compute the estimated physiological characteristic from the multi-dimensional representation.

17. The non-transitory computer readable storage medium of claim 15, wherein estimating the multi-dimensional representation comprises:
estimating a physiological characteristic value for each voxel in a three-dimensional (3D) representation based on relative contributions of the physiological characteristics from the plurality of channels of the optical sensor in accordance with expected distributions based on photon interactions within the tissue for the plurality of channels.

18. The non-transitory computer readable storage medium of claim 17, wherein the relative contributions of the physiological characteristics from the plurality of channels are weighted in accordance with quality metrics of the plurality of channels, and wherein the relative contributions of the physiological characteristics from the plurality of channels are estimated to constrain differences in the physiological characteristics between proximate voxels in the 3D representation.

19. The non-transitory computer readable storage medium of claim 15, wherein processing the multi-dimensional representation comprises:
thresholding a 3D representation to generate a binary 3D representation;
extracting features of the binary 3D representation; and
classifying whether the 3D representation includes the region that meets the one or more criteria using the extracted features.

20. The non-transitory computer readable storage medium of claim 19, wherein the features of the binary 3D representation include geometric features.

* * * * *